US012637682B2

(12) United States Patent
Yeo et al.

(10) Patent No.: US 12,637,682 B2
(45) Date of Patent: May 26, 2026

(54) PROTEIN TRANSLATIONAL CONTROL

(71) Applicant: The Regents of the University of California, Oakland, CA (US)

(72) Inventors: Eugene Yeo, La Jolla, CA (US); Frederick Tan, Encinitas, CA (US)

(73) Assignee: The Regents of the University of California

( * ) Notice: Subject to any disclaimer, the term of this patent is extended or adjusted under 35 U.S.C. 154(b) by 1189 days.

(21) Appl. No.: 17/604,139

(22) PCT Filed: Apr. 16, 2020

(86) PCT No.: PCT/US2020/028501
§ 371 (c)(1),
(2) Date: Oct. 15, 2021

(87) PCT Pub. No.: WO2020/214806
PCT Pub. Date: Oct. 22, 2020

(65) Prior Publication Data

US 2022/0204978 A1 Jun. 30, 2022

Related U.S. Application Data

(60) Provisional application No. 62/834,582, filed on Apr. 16, 2019.

(51) Int. Cl.
*C12N 15/67* (2006.01)
*C12N 9/22* (2006.01)
*C12N 15/11* (2006.01)

(52) U.S. Cl.
CPC ............... *C12N 15/67* (2013.01); *C12N 9/22* (2013.01); *C12N 15/111* (2013.01); *C07K 2319/09* (2013.01); *C12N 2310/20* (2017.05); *C12N 2310/317* (2013.01); *C12N 2750/14143* (2013.01)

(58) Field of Classification Search
CPC .............. A61K 31/713; A61K 2039/53; A61K 31/7105; A61K 31/711; A61K 31/712; C12Q 1/6806; C12Q 1/6809; C12Q 1/6869; C12Q 2525/179; C12Q 1/6844; C12Q 1/6813; C12Q 2525/186; C12Q 2563/179
USPC ........................................................ 435/69.1
See application file for complete search history.

(56) References Cited

U.S. PATENT DOCUMENTS 3,687,808 A 8/1972 Merigan et al.
5,034,506 A 7/1991 Summerton et al.
5,166,315 A 11/1992 Summerton et al.
5,185,444 A 2/1993 Summerton et al.
5,214,134 A 5/1993 Weis et al.
5,216,141 A 6/1993 Benner
5,235,033 A 8/1993 Summerton et al.
5,264,562 A 11/1993 Matteucci
5,264,564 A 11/1993 Matteucci
5,405,938 A 4/1995 Summerton et al.
5,434,257 A 7/1995 Matteucci et al.
5,466,677 A 11/1995 Baxter et al.
5,470,967 A 11/1995 Huie et al.
5,489,677 A 2/1996 Sanghvi et al.
5,539,082 A 7/1996 Nielsen et al.
5,541,307 A 7/1996 Cook et al.
5,561,225 A 10/1996 Maddry et al.
5,596,086 A 1/1997 Matteucci et al.
5,602,240 A 2/1997 De Mesmaeker et al.
5,608,046 A 3/1997 Cook et al.
5,610,289 A 3/1997 Cook et al.
5,618,704 A 4/1997 Sanghvi et al.
5,623,070 A 4/1997 Cook et al.
5,633,360 A 5/1997 Bischofberger et al.
5,663,312 A 9/1997 Chaturvedula
5,677,437 A 10/1997 Teng et al.
5,677,439 A 10/1997 Weis et al.
5,714,331 A 2/1998 Buchardt et al.
5,719,262 A 2/1998 Buchardt et al.
6,013,639 A * 1/2000 Peyman
6,461,864 B1 10/2002 Soriano et al.

(Continued)

FOREIGN PATENT DOCUMENTS

CA 3093580 A1 9/2019
CN 106103705 11/2016

(Continued)

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
Choudhury et al., "Engineering RNA endonucleases with customized sequence specificities," Nature communications, Oct. 23, 2012, 3(1):1-18.
Hwang et al., "Efficient genome editing in zebrafish using a CRISPR-Cas system," Nature biotechnology, Mar. 2013, 31(3):227-229.

(Continued)

*Primary Examiner* — Tekchand Saidha
*Assistant Examiner* — Mohammad Y Meah
(74) *Attorney, Agent, or Firm* — Fish & Richardson P.C.

(57) ABSTRACT

Provided herein are compositions and methods for regulating protein translation. The compositions include a cap-conjugated oligonucleotide comprising an m7G cap or a variant or analog thereof conjugated to an oligonucleotide, wherein the oligonucleotide is capable of specifically hybridizing with a target sequence in an RNA molecule. The disclosure further provides methods of regulating translation of an mRNA in a cell, the method comprising contacting the cell with a cap-conjugated oligonucleotide comprising an m7G cap or a variant or analog thereof conjugated to an oligonucleotide, wherein the oligonucleotide comprises a sequence capable of specifically hybridizing with a target sequence in an RNA molecule.

24 Claims, 1 Drawing Sheet

(56) References Cited

U.S. PATENT DOCUMENTS

| | | | |
|---|---|---|---|
| 6,471,996 | B1 | 10/2002 | Sokoll et al. |
| 6,472,375 | B1 | 10/2002 | Hoon et al. |
| 7,074,596 | B2 | 7/2006 | Darzynkiewicz et al. |
| 7,078,387 | B1 | 7/2006 | Leiden et al. |
| 8,304,529 | B2 | 11/2012 | Kore et al. |
| 8,697,359 | B1 | 4/2014 | Zhang |
| 9,074,199 | B1 | 7/2015 | Chavez et al. |
| 10,913,768 | B2 * | 2/2021 | Hogrete |
| 11,453,891 | B2 | 9/2022 | Yeo et al. |
| 11,667,903 | B2 | 6/2023 | Yeo et al. |
| 2002/0068709 | A1 | 6/2002 | Orum et al. |
| 2015/0056702 | A1 | 2/2015 | Conway |
| 2015/0056705 | A1 | 2/2015 | Conway et al. |
| 2015/0071899 | A1 | 3/2015 | Liu et al. |
| 2015/0232844 | A1 * | 8/2015 | Ozsolak et al. |
| 2015/0353905 | A1 | 12/2015 | Weiss |
| 2016/0138012 | A1 | 5/2016 | Wickens et al. |
| 2016/0214276 | A1 | 7/2016 | Liu |
| 2016/0215276 | A1 | 7/2016 | Liu et al. |
| 2016/0238593 | A1 | 8/2016 | Biyden et al. |
| 2016/0289659 | A1 | 10/2016 | Doudna et al. |
| 2016/0304846 | A1 | 10/2016 | Liu et al. |
| 2016/0362667 | A1 | 12/2016 | Donohue et al. |
| 2017/0073670 | A1 | 3/2017 | Nishida et al. |
| 2017/0306335 | A1 | 10/2017 | Zhang et al. |
| 2018/0073012 | A1 | 3/2018 | Liu et al. |
| 2018/0208924 | A1 | 7/2018 | Fukuda et al. |
| 2018/0273576 | A1 * | 9/2018 | Hogfree et al. |
| 2019/0062724 | A1 | 2/2019 | Hsu et al. |
| 2020/0239863 | A1 | 7/2020 | Yeo |
| 2020/0248169 | A1 | 8/2020 | Zhang et al. |
| 2021/0079366 | A1 | 3/2021 | Zhang et al. |
| 2021/0332344 | A1 | 10/2021 | Yeo et al. |
| 2021/0340197 | A1 | 11/2021 | Yeo et al. |
| 2022/0127621 | A1 | 4/2022 | Yeo et al. |
| 2022/0220473 | A1 | 7/2022 | Yeo et al. |
| 2023/0053915 | A1 | 2/2023 | Yeo et al. |
| 2023/0365951 | A1 | 11/2023 | Yeo et al. |

FOREIGN PATENT DOCUMENTS

| | | | | |
|---|---|---|---|---|
| CN | 108103090 | | 6/2018 | |
| CN | 110055284 | | 7/2019 | |
| JP | 2015-506669 | | 3/2015 | |
| JP | 2019-500899 | A | 1/2019 | |
| WO | WO 1998/39352 | | 9/1998 | |
| WO | WO 1999/14226 | | 3/1999 | |
| WO | WO 2000/066604 | | 11/2000 | |
| WO | WO-2007123579 | A2 * | 11/2007 | ......... A61K 31/7056 |
| WO | WO 2009/066758 | | 5/2009 | |
| WO | WO 2009/149253 | | 12/2009 | |
| WO | WO 2001/75097 | | 10/2011 | |
| WO | WO 2012/068627 | | 5/2012 | |
| WO | WO 2013/058404 | | 4/2013 | |
| WO | WO 2013/082548 | | 6/2013 | |
| WO | WO 2013/130684 | | 9/2013 | |
| WO | WO 2014/093622 | | 6/2014 | |
| WO | WO 2014/093635 | | 6/2014 | |
| WO | WO 2014/093661 | | 6/2014 | |
| WO | WO 2014/113493 | | 7/2014 | |
| WO | WO 2014/191518 | | 12/2014 | |
| WO | WO 2014/191521 | | 12/2014 | |
| WO | WO 2015/006294 | | 1/2015 | |
| WO | WO 2015/048690 | | 4/2015 | |
| WO | WO 2015/089277 | | 6/2015 | |
| WO | WO 2015/089351 | | 6/2015 | |
| WO | WO 2015/089354 | | 6/2015 | |
| WO | WO 2016/019655 | | 2/2016 | |
| WO | WO 2016/097212 | | 6/2016 | |
| WO | WO 2016/106236 | | 6/2016 | |
| WO | WO 2016/183402 | | 11/2016 | |
| WO | WO 2016/191684 | | 12/2016 | |
| WO | WO 2016/196655 | | 12/2016 | |
| WO | WO 2016/196805 | | 12/2016 | |
| WO | WO 2016/201138 | | 12/2016 | |
| WO | WO 2017/010556 | | 1/2017 | |
| WO | WO 2017/053297 | | 3/2017 | |
| WO | WO 2017/053312 | | 3/2017 | |
| WO | WO 2017/091630 | | 6/2017 | |
| WO | WO 2017/219027 | | 12/2017 | |
| WO | WO 2018/002697 | | 1/2018 | |
| WO | WO 2018/027078 | | 2/2018 | |
| WO | WO 2018/075827 | | 4/2018 | |
| WO | WO 2018/154387 | | 8/2018 | |
| WO | WO 2018/183703 | | 10/2018 | |
| WO | WO 2019/006471 | | 1/2019 | |
| WO | WO 2019/040664 | | 2/2019 | |
| WO | WO 2019/060746 | | 3/2019 | |
| WO | WO 2019/204828 | | 10/2019 | |

OTHER PUBLICATIONS

Kanadia et al., "A muscleblind knockout model for myotonic dystrophy," Science, Dec. 12, 2003, 302(5652):1978-1980.

Koren et al., "Cell-penetrating peptides: breaking through to the other side," Trends in molecular medicine, Jul. 1, 2012, 18(7):385-393.

Long et al., "Postnatal genome editing partially restores dystrophin expression in a mouse model of muscular dystrophy," Science, Jan. 22, 2016, 351(6271):400-403.

Miyanohara et al., "Potent spinal parenchymal AAV9-mediated gene delivery by subpial injection in adult rats and pigs," Molecular Therapy-Methods & Clinical Development, Jan. 1, 2016, 3:16046, 10 pages.

Mouisel et al., "Outcome of acetylcholinesterase deficiency for neuromuscular functioning," Neuroscience research, Aug. 1, 2006, 55(4):389-396.

Nishimasu, et al. "Crystal structure of Cas9 in complex with guide RNA and target DNA," Cell, Feb. 27, 2014, 156(5):935-949.

Orengo et al., "Expanded CTG repeats within the DMPK 3' UTR causes severe skeletal muscle wasting in an inducible mouse model for myotonic dystrophy," Proceedings of the National Academy of Sciences, Feb. 19, 2008, 105(7):2646-2651.

TransIT-LT1 Transfection Reagent Data Sheet, Mirus Bio, 2017, 6 pages.

Wheeler et al., "Correction of ClC-1 splicing eliminates chloride channelopathy and myotonia in mouse models of myotonic dystrophy," The Journal of clinical investigation, Dec. 3, 2007, 117(12):3952-3957.

Yang et al., "A dual AAV system enables the Cas9-mediated correction of a metabolic liver disease in newborn mice," Nature biotechnology, Mar. 2016, 34(3):334-338.

Zuris et al., "Cationic lipid-mediated delivery of proteins enables efficient protein-based genome editing in vitro and in vivo," Nature biotechnology, Jan. 2015, 33(1):73-80.

Adamala et al., "Programmable RNA-binding protein composed of repeats of a single modular unit," Proceedings of the National Academy of Sciences, May 10, 2016, 113(19):E2579-E2588.

Akerstrom et al., "A physicochemical study of protein G, a molecule with unique immunoglobulin G-binding properties, " J. Biol. Chem., 1986, 261: 10,240-10,247.

Allocca et al., "Novel adeno-associated virus serotypes efficiently transduce murine photoreceptors," Journal of virology, Oct. 15, 2007, 81(20):11372-11380.

Anant et al., "Molecular mechanisms of apolipoprotein B mRNA editing,"Current opinion in lipidology, Apr. 1, 2001, 12(2):159-165.

Asokan et al., "The AAV vector toolkit: poised at the clinical crossroads," Molecular Therapy, Apr. 1, 2012, 20(4):699-708.

Bashor et al., "Using engineered scaffold interactions to reshape MAP kinase pathway signaling dynamics," Science, 2008, 319(5869):1539-1543.

Basolo et al., "RET protein expression has no prognostic impact on the long-term outcome of papillary thyroid carcinoma," European journal of endocrinology, Nov. 1, 2001, 145(5):599-604.

Batra et al., "Elimination of Toxic Microsatellite Repeat Expansion RNA by RNA-Targeting Cas9," Cell, 2017, 170(5):889-912.e10, 34 Pages.

(56) References Cited

OTHER PUBLICATIONS

Batra et al., "Loss of MBNL Leads to Disruption of Developmentally Regulated Alternative Polyade in RNA-Mediated Disease," Mol. Cell, Oct. 2014, 56(2):311-322.
Bennett et al., "RNA targeting therapeutics: molecular mechanisms of antisense oligonucleotides as a therapeutic platform," Anmi Rev Pharmacol Toxlcol, 2010, 50: 259-293.
Bertrand et al., "Localization of ASHI mRNA particles in living yeast," Molecular cell, Oct. 1, 1998, 2(4):437-445.
Beuth et al., "Structure of a Mycobacterium tuberculosis NusA—RNA complex," The EMBO journal, Oct. 19, 2005, 24(20):3576-3587.
Bjerke et al., "Recent Advances in CRISPR Base Editing: From A to RNA," Biochemistry, Jan. 26, 2018, vol. 57, pp. 886887.
Bjorck et al., "Purification and some properties of streptococcal protein G, a novel IgG-binding reagent," J. Immunol., 1984, 133:969-974.
Blanc et al., "C-to-U RNA editing: mechanisms leading to genetic diversity," Journal of Biological Chemistry, Jan. 17, 2003, 278(3):1395-1398.
Borghardt et al., "Inhaled Therapy in Respiratory Disease: The Complex Interplay of Pulmonary Kinetic Processes," Canadian Respiratory Journal, 2018, 1-11.
Braasch et al., "Novel antisense and peptide nucleic acid strategies for controlling gene expression," Biochemistry, Apr. 9, 2002,41(14):4503-4510.
Braddock et al., "Structure and dynamics of KH domains from FBP bound to single-stranded DNA," Nature, Feb. 2002, 415(6875):1051-1056.
Brezgin et al., "Dead Cas systems: types, principles, and applications," International journal of molecular sciences, Jan. 2019, 20(23):6041, 26 pages.
Buchan et al., "Eukaryotic stress granules: the ins and outs of translation," Molecular cell, Dec. 24, 2009, 36(6):932-941.
Buxbaum et al., "Single β-actin mRNA detection in neurons reveals a mechanism for regulating its translatability," Science, Jan. 24, 2014, 343(6169): 5 Pages.
Cai et al., "Quantitative assessment of mRNA cap analogues as inhibitors of in vitro translation," Biochemistry, Jun. 29, 1999, 38(26):8538-8547.
Cao et al., "A universal strategy for regulating mRNA translation in prokaryotic and eukaryotic cells," Nucleic acids research, Apr. 30, 2015 43(8):4353-4362.
Cencic et al., "Protospacer adjacent motif (PAM)-distal sequences engage CRISPR Cas9 DNA target cleavage," PloS one, Oct. 2, 2014, 9(10):e109213, 13 Pages.
Chen et al., "Dynamic imaging of genomic loci in living human cells by an optimized CRISPR/Cas system," Cell, Dec. 19, 2013, 155(7):1479-1491.
Chen et al., "Structure-guided design, synthesis, and evaluation of guanine-derived inhibitors of the eIF4E mRNA-cap interaction," Journal of medicinal chemistry, Apr. 26, 2012, 55(8):3837-3851.
Cheong et al., "Engineering RNA sequence specificity of Pumilio repeats," Proceedings of the National Academy of Sciences, Sep. 12, 2006, 103(37):13635-13639.
Cho et al., "Targeted genome engineering in human cells with the Cas9 RNA-guided endonuclease," Nature biotechnology, Mar. 2013, 31(3): 230-232.
Chou et al., "Picky: oligo microarray design for large genomes," Bioinformatics, 2004, 20(17):2893-28902.
Cichowski et al., "NF1 tumor suppressor gene function: narrowing the GAP," Cell, Feb. 23, 2001, 104(4):593-604.
Cokol et al., "Finding nuclear localization signals, " EMBO reports, Nov. 1, 2000, 1(5):411-415.
Cong et al., "Multiplex genome engineering LJsing CRISPR/Cas systems," Science, Feb. 15, 2013, 339(6121): 6 Pages.
Cooke et al., "Targeted translational regulation using the PUF protein family scaffold," Proceedings of the National Academy of Sciences, Sep. 20, 2011, 108(38):15870-15875.
Cox et al., "RNA editing with CRISPR_Cas13," Science, 2017, 358(6366):1019-1027.
De Mesmaeker et al., "Antisense oligonucleotides," Accounts of Chemical Research, Sep. 1, 1995, 28(9):366-374.
De Zoysa et al., "Posttranscriptional RNA pseudouridylation," The enzymes, Jan. 1, 2017, 41:151-167.
Deer et al., "High-level expression of proteins in mammalian cells using transcription regulatory sequences from the Chinese hamster EF-1α gene," Biotechnology progress, 2004, 20(3):880-889.
DeJesus-Hernandez et al., "Expanded GGGGCC hexanucleotide repeat in noncoding region of C9ORF72 causes chromosome 9p-linked FTD and ALS," Neuron, Oct. 20, 2011, 72(2): 245-256.
Delebecque et al., "Organization of intracellular reactions with rationally designed RNA assemblies," Science, Jul. 22, 2011 333(6041): 7 Pages.
Deyle et al., "Adeno-associated virus vector integration," Current opinion in molecular therapeutics, Aug. 2009, 11(4):442-447.
Doench et al., "Rational design of highly active sgRNAs for CRISPR-Cas9-mediated gene inactivation," Nature biotechnology, 2014, 32(12): 8 Pages.
Dong et al., "Quantitative analysis of the packaging capacity of recombinant adeno-associated virus," Human gene therapy, Nov. 10, 1996, 7(17):2101-2112.
Donnelly et al., "Limited availability of ZBP1 restricts axonal mRNA localization and nerve regeneration capacity," The EMBO journal, Nov. 16, 2011, 30(22):4665-4677.
Dow et al., "Inducible in vivo genome editing with CRISPR-Cas9," Nature biotechnology, Apr. 2015, 33(4): 7 Pages.
Du et al., "m 6 A RNA methylation controls neural development and is involved in human diseases," Molecular neurobiology, Mar. 2019, 56(3):1596-1606.
Dueber et al., "Synthetic protein scaffolds provide modular control over metabolic flux," Nature biotechnology, Aug. 2009, 27(8): 9 Pages.
Durand et al., "The inside out of lentiviral vectors," Viruses, Feb. 2011, 3(2):132-159.
Durocher et al., "High-level and high-throughput recombinant protein production by transient transfection of suspension-growing human 293-EBNA1 cells," Nucleic Acids Research, 2002, 30(2), 9 pages.
Eliasson et al., "Chimeric IgG-binding receptors engineered from staphylococcal protein A and streptococcal protein G," J. Biol. Chem., 1988, 263:4323-4327.
Encode Project ConsortiL.1m, The; "An integrated encyclopedia of ONA elements in the human genome," Nature, 2012, 489(7414): 57-74.
Englisch et al., "Chemically modified oligonucleotides as probes and inhibitors," Angewandte Chemie International Edition in English, Jun. 1991, 30(6):613-629.
Esakova et al., "Of proteins and RNA: the RNase P/MRP family," Rna, Sep. 1, 2010, 16(9):1725-1747.
Esvelt et al., "Orthogonal Cas9 proteins for RNA-guided gene regulation and editing," Nature methods, Nov. 2013, 10(11): 8Pages.
Extended European Search Report in EP Appln. No. 18799398, dated May 15, 2020, 11 pages.
Extended European Search Report in EP Appln. No. 19788702.9, dated Oct. 13, 2021, 11 pages.
Fernanda et al., "Current strategies for site-directed RNA editing using ADARs," Methods, 2018, 156:16-24.
Filipovska et al., "A universal code for RNA recognition by PUF proteins," Nature chemical biology, Jul. 2011, 7(7): 4 Pages.
Fouts et al., "Functional recognition of fragmented operator sites by R17/MS2 coat protein, a translational repressor," Nucleic acids research, Nov. 1, 1997, 25(22):4464-4473.
Freitas et al., "Mechanisms and signals for the nuclear import of proteins," Current genomics, Dec. 2009, 10(8):550-557.
Fu et al., "Improving CRISPR-Cas nuclease specificity using truncated guide RNAs," Nature biotechnology, Mar. 2014, 32(3): 8 Pages.
Fukuda et al., "Construction of a guide-RNA for site-directed RNA mutagenesis utilising intracellular A-to-I RNA editing," Sci Rep, 2017, 7:41478.

(56) References Cited

OTHER PUBLICATIONS

Fusco et al., Single mRNA molecules demonstrate probabilistic movement in living mammalian cells, Current Biology, Jan. 21, 2003, 13(2):161-167.
Garcia et al., "MS2 coat proteins bound to yeast mRNAs block 5' to 3' degradation and trap mRNA decay products: implications for the localization of mRNAs by MS2-MCP system," Rna, Aug. 1, 2015, 21(8): 4 Pages.
Gebeyehu et al., "Novel biotinylated nucleotide-analogs for labeling and colorimetric detection of DNA," Nucleic acids research, Jun. 11, 1987, 15(11):4513-4534.
Geisler et al., "RNA in unexpected places: long non-coding RNA functions in diverse cellular contexts," Nature reviews Molecular cell biology, Nov. 2013, 14(11): 14 Pages.
GenBank Accession No. FJ209302, "*Homo sapiens* MALAT1-associated small cytoplasmic RNA, complete sequence," Dec. 2, 2008, 1 page.
GenBank Accession No. NM_019852.4, "*Homo sapiens* methyltransferase like 3 (METTL3), mRNA," Oct. 21, 2018, 6 pages.
Gentz et al., "Bioassay for trans-activation using purified human immunodeficiency virus tat-encoded protein: trans-activation requires mRNA synthesis, " Proc. Natl. Acad. Sci., 1989, 86:821-824.
German-Retana et al., "Mutational analysis of plant cap-binding protein eIF4E reveals key amino acids involved in biochemical functions and potyvirus infection," Journal of virology, Aug. 1, 2008, 82(15):7601-7612.
Gerstberger et al., "Evolutionary conservation and expression of human RNA-binding proteins and their role in human genetic disease," InSystems biology of RNA binding proteins, 2014 pp. 1-55.
Gilbert et al., "CRISPR-mediated modular RNA-guided regulation of transcription in eukaryotes," Cell, Jul. 18, 2013, 154(2):442-451.
Graham et al., "Resources for the design of CRISPR gene editing experiments," Genome Biol., 2015, 16(1):260.
Graveley et al., "Arginine/serine-rich domains of SR proteins can function as activators of pre-mRNA splicing," Molecular cell, Apr. 1, 1998, 1(5):765-771.
Gritsenko et al., "Sequence features of viral and human Internal Ribosome Entry Sites predictive of their activity," PLoS computational biology, Sep. 18, 2017, 13(9):e1005734, 23 Pages.
Guss et al., "Structure of the IgG-binding regions of streptococcal protein G," EMBO J., 1986, 5:1567-1575.
Guzzi et al., "Pseudouridylation of tRNA-derived fragments steers translational control in stem cells," Cell, May 17, 2018, 173(5): 40 pages.
Hale et al., "RNA-guided RNA cleavage by a CRISPR RNA-Cas protein complex," Cell, Nov. 25, 2009, 139(5):945-956.
Halo et al., "NanoFlares for the detection, isolation, and culture of live tumor cells from human blood," PNAS, 2014, 111(48):17104-17109.
Hamajima et al., "Intranasal administration of HIV-DNA vaccine formulated with a polymer, carboxymethylcellulose, augments mucosal antibody production and cell-mediated immune response," Clinical immunology and immunopathology, Aug. 1, 1998, 88(2):205-210.
Hanswillemenke et al., "Site-Directed RNA Editing in Vivo Can Be Triggered by the Light-Driven Assembly of an Artificial Riboprotein," J Am Chem Soc, 2015, 137(50):15875-81.
Heasman, "Morpholino oligos: making sense of antisense?" Developmental biology, Mar. 15, 2002, 243(2):209-214.
Hendel et al., "Chemically modified guide RNAs enhance CRISPR-Cas genome editing in human primary cells," Nature biotechnology, Jun. 29, 2015, 33(9):985-989.
Hermonat & Muzyczka, "Use of adeno-associated virus as a mammalian DNA cloning vector: transduction of neomycin resistance into mammalian tissue culture cells," Proc. Natl. Acad. Sci. USA, 1984, 81:6466-6470.
Higuchi et al., "RNA editing of AMPA receptor subunit GluR-B: a base-paired intron-exon structure determines position and efficiency," Cell, 1993, 75(7):1361-70.
Hjelm et al., "Immunologically active and structurally similar fragments of protein A from *Staphylococcus aureus*," Eur. J. Biochem., 1975, 57:395-403.
Ho et al., "Colocalization of muscleblind with RNA foci is separable from mis-regulation of alternative splicing in myotonic dystrophy," Journal of cell science, Jul. 1, 2005, 118(13):2923-2933.
Hsu et al., "Development and applications of CRISPR-Cas9 for genome engineering," Cell, 2014, 156(6):1262-1278.
Hua et al., "Antisense correction of SMN2 splicing in the CNS rescues necrosis in a type III SMA mouse model," Genes & development, Aug. 1, 2010, 24(15):1634-1644.
Hua et al., "Antisense masking of an hnRNP A1/A2 intronic splicing silencer corrects SMN2 splicing in transgenic mice," The American Journal of Human Genetics, Apr. 11, 2008, 82(4):834-848.
Hua et al., Peripheral SMN restoration is essential for long-term rescue of a severe spinal muscular atrophy mouse model, Nature, Oct. 2011, 478(7367):123-126.
Huang et al., "Inducing nonsense suppression by targeted pseudouridylation," nature protocols, Apr. 2012, 7(4):789-800.
Hwang et al., "Efficient in vivo genome editing using RNA-guided nucleases," Nature biotechnology, Mar. 2013, 31(3): 12 Pages.
International Preliminary Report on Patentability in International Appln. No. PCT/US2018/031913, dated Nov. 12, 2019, 10 pages.
International Preliminary Report on Patentability in International Appln. No. PCT/US2019/028580, dated Oct. 29, 2020, 9 pages.
International Preliminary Report on Patentability in International Appln. No. PCT/US2019/049182, dated Mar. 11, 2021, 7 pages.
International Preliminary Report on Patentability in International Appln. No. PCT/US2019/049197, dated Mar. 11, 2021, 9 pages.
International Preliminary Report on Patentability in International Appln. PCT /US2020/028501, dated Oct. 28, 2021, 10 pages.
International Preliminary Report on Patentability in International Appln. PCT/US2020/028546, dated Oct. 28, 2021, 11 pages.
International Search Report and Written Opinion in International Appln. PCT/US2018/031913, dated Aug. 2, 2018, 4 pages.
International Search Report and Written Opinion in International Appln. PCT/US2016/063429 dated May 8, 2017; 21 pages.
International Search Report and Written Opinion in International Appln. No. PCT/US2019/028580, dated Aug. 27, 2019, 14 pages.
International Search Report and Written Opinion in International Appln. No. PCT/US2019/049182, dated Dec. 6, 2019, 11 pages.
International Search Report and Written Opinion in International Appln. No. PCT/US2019/049197, dated Dec. 12, 2019, 12 pages.
Jia et al., "N 6-methyladenosine in nuclear RNA is a major substrate of the obesity-associated FTO," Nature chemical biology, Dec. 2011, 7(12):885-887.
Jiang F, "Structures of a CRISPR-Cas9 R-loop complex primed for DNA cleavage," Science, 2016, 351(6275): 9 Pages.
Jinek et al., "A programmable dual RNA-guided DNA endonuclease in adaptive bacterial immunity," Science, 2012, 337(6096): 14 Pages.
Jinek et al., "RNA-programmed genome editing in human cells," elife, Jan. 29, 2013, 2:e00471, 9 Pages.
Kadokura et al., "Solid-phase synthesis of a 5'-terminal TMG-capped trinucleotide block of U1 snRNA," Tetrahedron Letters, Dec. 10, 2001, 42(50):8853-8856.
Karijolich et al., "Converting nonsense codons into sense codons by targeted pseudouridylation," Nature, Jun. 2011, 474(7351):395-398.
Karijolich et al., "Transcriptome-wide dynamics of RNA pseudouridylation," Nature reviews Molecular cell biology, Oct. 2015, 16(10): 5 pages.
Kedersha et al., "Mammalian stress granules and processing bodies," Methods in enzymology, Jan. 1, 2007, 431:61-81.
Kelley et al., "Versatility of chemically synthesized guide RNAs for CRISPR-Cas9 genome editing," J. of Biotechnology, 2016, 233:25 Pages.
Khani et al., "AAV-mediated expression targeting of rod and cone photoreceptors with a human rhodopsin kinase promoter," Investigative ophthalmology & visual science, Sep. 1, 2007, 48(9):3954-3961.
Kirsebom, "RNase P RNA mediated cleavage: substrate recognition and catalysis," Biochimie, Oct. 1, 2007, 89(10):1183-1194.

(56) References Cited

OTHER PUBLICATIONS

Kislauskis et al., "Sequences responsible for intracellular localization of beta-actin messenger RNA also affect cell phenotype," The Journal of cell biology, Oct. 15, 1994, 127(2):441-451.
Kodama et al., "An improved bimolecular fluorescence complementation assay with a high signal-to-noise ratio," Biotechniques, 2010, 49(5):793-805.
Konermann et al., "Genome-scale transcriptional activation by an engineered CRISPR-Cas9 complex," Nature, 2015, 517(7356):583-588.
Konermann et al., "Transcriptome engineering with RNA-targeting type VI-D Crispr effectors," Cell, Apr. 19, 2018, 173(3): 27 Pages.
Kormann et al., "Expression of therapeutic proteins after delivery of chemically modified mRNA in mice," Nature biotechnology, Feb. 2011, 29(2):154-157.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, Apr. 2, 1998, 54(14):3607-3630.
Kotterman et al., "Viral Vectors for Gene Therapy: Translational and Clinical Outlook," Annual Review of Biomedical Engineering, 2015, 17:63-89.
Kuscu et al., "Genome-wide analysis reveals characteristics of off-target sites bound by the Cas9 endonuclease," Nature biotechnology, Jul. 2014, 32(7): 9 Pages.
Kuttan & Bass, "Mechanistic insights into editing-site specificity of ADARs," PNAS, 2012, 109(48):E3295-E3304.
Lacerra et al., "Restoration of hemoglobin A synthesis in erythroid cells from peripheral blood of thalassemic patients," Proceedings of the National Academy of Sciences, Aug. 15, 2000, 97(17):9591-9596.
Lai et al., "Unexpected diversity of RNase P, an ancient tRNA processing enzyme: challenges and prospects," FEBS letters, Jan. 21, 2010, 584(2):287-296.
Laird-Offringa et al., "Analysis of RNA-binding proteins by in vitro genetic selection: identification of an amino acid residue important for locking U1A onto its RNA target," Proceedings of the National Academy of Sciences, Dec. 5, 1995, 92(25):11859-11863.
Lebkowski et al., "Adeno-associated virus: a vector system for efficient introduction and integration of DNA into a variety of mammalian cell types, " Mol. Cell. Biol., 1988, 8:3988-3996.
Li et al., "Heritable gene targeting in the mouse and rat using a CRISPR-Cas system," Nature biotechnology, Aug. 2013, 31(8):681-683.
Li et al., "Stress granules as crucibles of ALS pathogenesis," Journal of cell biology, Apr. 29, 2013, 201(3):361-372.
Li et al., "Targeted mRNA demethylation using an engineered dCas13b-ALKBH5 fusion protein," Nucleic acids research, Jun. 4, 2020, 48(10):5684-5694.
Lionnet et al., "A transgenic mouse for in vivo detection of endogenous labeled mRNA," Nature methods, Feb. 2011, 8(2): 9 Pages.
Lovci et al., "Rbfox proteins regulate alternative mRNA splicing through evolutionarily conserved RNA bridges," Nature structural & molecular biology, Dec. 2013, 20(12): 11 Pages.
Lu et al., "MicroRNA expression profiles classify human cancers," nature, Jun. 2005, 435(7043):834-838.
MacKenzie et al., "Stromal expression of miR-21 identifies high-risk group in triple-negative breast cancer," The American journal of pathology, Dec. 1, 2014, 184(12):3217-3225.
Maddalo et al., "In vivo engineering of oncogenic chromosomal rearrangements with the CRISPR/Cas9 system," Nature, Dec. 2014, 516(7531): 15 Pages.
Maity et al., "N6-methyladenosine modification in mRNA: machinery, function and implications for health and diseases," The FEBS journal, May 2016, 283(9):1607-1630.
Mali et al., "CAS9 transcriptional activators for target specificity screening and paired nickases for cooperative genome engineering," Nature biotechnology, Sep. 2013, 31(9): 8 Pages.
Mali et al., "RNA-guided human genome engineering via Cas9," Science, Feb. 15, 2013, 339(6121): 5 Pages.
Manders et al., "Dynamics of three-dimensional replication patterns during the S-phase, analysed by double labelling of DNA and confocal microscopy," Journal of cell science, Nov. 1, 1992, 103(3):857-862.
Martin, "Ein neuer Zugang zu 2'-O-Alkylribonucleosiden und Eigenschaften deren Oligonucleotide," Helvetica Chimica Acta, Mar. 22, 1995, 78(2):486-504.
Massie et al., "Inducible overexpression of a toxic protein by an adenovirus vector with a tetracycline-regulatable expression cassette," Journal of Virology, Mar. 1, 1998, 72(3):2289-2296.
Matthews et al., "Structures of human ADAR2 bound to dsRNA reveal base-flipping mechanism and basis for site selectivity," Nature structural & molecular biology, May 2016, 23(5): 23 Pages.
McMahon et al., "TRIBE: Hijacking an RNA-Editing Enzyme to Identify Cell-Specific Targets of RNA-Binding Proteins," Cell, 2016, 165(3):742-53.
Meng et al., "Towards a therapy for Angelman syndrome by targeting a long non-coding RNA," Nature, Feb. 2015, 518(7539): 16 Pages.
Mingozzi et al., "Therapeutic in vivo gene transfer for genetic disease using AAV: progress and challenges," Nature reviews genetics, May 2011, 12(5):341-355.
Mohr et al., "CRISPR guide RNA design for research applications," FEBS Journal, 2016, 283(17):3232-3238.
Montiel-Gonzalez et al "An efficient system for selectively altering genetic information within mRNAs." Nucleic Acids Res., 2016, 44:e157.
Montiel-Gonzalez et al., "Correction of mutations within the cystic fibrosis transmembrane conductance regulator by site-directed RNA editing." PNAS, 2013, 110(45):18285-90.
Muddashetty et al., "Reversible inhibition of PSD-95 mRNA translation by miR-125a, FMRP phosphorylation, and mGluR signaling," Molecular cell, Jun. 10, 2011, 42(5):673-688.
Mukhopadhyay et al., "C→ U editing of neurofibromatosis 1 mRNA occurs in tumors that express both the type II transcript and apobec-1, the catalytic subunit of the apolipoprotein B mRNA-editing enzyme," The American Journal of Human Genetics, Jan. 1, 2002, 70(1):38-50.
Muzyczka, "Use of adeno-associated virus as a general transduction vector for mammalian cells," Viral expression vectors, 1992, 97-129.
Nakayama et al., "Simple and efficient CRISPR/Cas9-mediated targeted mutagenesis in Xenopus tropicalis," genesis, Dec. 2013, 51(12):835-843.
Nasevicius et al., "Effective targeted gene 'knockdown' in zebrafish," Nature genetics, Oct. 2000, 26(2):216-220.
Nelles et al., "Applications of Cas9 as an RNA-programmed RNA-binding protein," BioEssays, Jul. 2015, 37(7): 8 Pages.
Nelles et al., "Programmable RNA tracking in live cells with CRISPR/Cas9," Cell, Apr. 7, 2016, 165(2): 10 Pages.
Nielsen "Sequence-selective recognition of DNA by strand displacement with a thymine-substituted polyamide, " Science, Dec. 6, 1991, 254(5037):1497-1500.
Nishikura, "A-to-I editing of coding and non-coding RNAs by ADARs," Nat Rev Mol Cell Biol, 2016, 17(2):83-96.
Nissim-Rafinia et al., "Splicing regulation as a potential genetic modifier," TRENDS in Genetics, Mar. 1, 2002, 18(3):123-127.
O'Connell et al., "Programmable RNA recognition and cleavage by CRISPR/Cas9," Nature., 2014, 516(7530): 23 Pages.
Ohkubo et al., "Efficient solid-phase synthesis of oligodeoxynucleotides having a 5'-terminal 2, 2, 7-trimethylguanosine pyrophosphate linkage," Bioorganic & medicinal chemistry, Jul. 1, 2009, 17(13):4819-4824.
O'Keefe et al., "Scaleable manufacture of HIV-1 entry inhibitor griffithsin and validation of its safety and efficacy as a topical microbicide component," Proc. Nat. Acad. Sci. USA, 2009, 106(15):6099-6104.
Ozawa et al., "Imaging dynamics of endogenous mitochondrial RNA in single living cells," Nature methods, May 2007, 4(5):413-419.
Paige et al., "RNA mimics of green fluorescent protein," Science, Jul. 29, 2011, 333(6042): 35 Pages.

(56) References Cited

OTHER PUBLICATIONS

Pang et al., "Comparative analysis of in vivo and in vitro AAV vector transduction in the neonatal mouse retina: effects of serotype and site of administration," Vision research, Feb. 1, 2008, 48(3):377-385.
Park et al., "Visualization of dynamics of single endogenous mRNA labeled in live mouse," Science, Jan. 24, 2014, 343(6169):422-424.
Partial International Search Report for International Application No. PCT/US2016/063429, dated Feb. 28, 2017 11 pages.
Pasca et al. "Using iPSC-derived neurons to uncover cellular phenotypes associated with Timothy syndrome," Nat Med, 2011, 17(12):18 Pages.
Passini et al., "Antisense oligonucleotides delivered to the mouse CNS ameliorate symptoms of severe spinal muscular atrophy," Science translational medicine, Mar. 2, 2011, 3(72):72ra18, 11 Pages.
Phelps et al., "Recognition of duplex RNA by the deaminase domain of the RNA editing enzyme ADAR2," Nuc. Acid Res., 2015, 43(2):1123-1132.
Price et al., "Cas9-mediated targeting of viral RNA in eukaryotic cells," Proceedings of the National Academy of Sciences, May 12, 2015, 112(19): 14 Pages.
Qi et al., "Repurposing CRISPR as an RNA-guided platform for sequence-specific control of gene expression," Cell, Feb. 28, 2013, 152(5):1173-1183.
Rackham et al., "Visualization of RNA-protein interactions in living cells: FMRP and IMP1 interact on mRNAs, " The EMBO journal, Aug. 18, 2004, 23(16):3346-3355.
Rahdar et al., "Synthetic CRISPR RNA-Cas9-guided genome editing in human cells," Proceedings of the National Academy of Sciences, Dec. 22, 2015, 112(51):E7110-7117.
Rath et al., "Genetically encoded tools for RNA imaging in living cells," Current opinion in biotechnology, Feb. 1, 2015, 31:42-49.
Renton et al., "A hexanucleotide repeat expansion in C9ORF72 is the cause of chromosome 9p21-linked ALS-FTD," Neuron., Oct. 20, 2011, 72(2):257-268.
Sachdeva et al., "In vivo co-localization of enzymes on RNA scaffolds increases metabolic production in a geometrically dependent manner," Nucleic acids research, Aug. 18, 2014, 42(14):9493-9503.
Sampson et al., "A CRISPR/Cas system mediates bacterial innate immune evasion and virulence," Nature, May 2013, 497(7448): 5 Pages.
Sander et al., "CRISPR-Cas systems for editing, regulating and targeting genomes," Nature biotechnology, Apr. 2014, 32(4):347-355.
Schellenberger et al., "A recombinant polypeptide extends the in vivo half-life of peptides and proteins in a tunable manner," Nat Biotechnol., 2009, 27(12):1186-1190.
Schindelin et al., "Fiji: an open-source platform for biological-image analysis," Nature methods, Jul. 2012, 9(7):676-682.
Schlesinger & Dubensky, "Alphavirus vectors for gene expression and vaccines," Curr. Opin. Biotechnol., 1999, 10(5):434-439.
Schneider et al "Optimal guideRNAs for re-directing deaminase activity of hADARI and hADAR2 in trans." Nucleic Acids Res., 2014, 42:e87.
Shestakova et al., "The physiological significance of β-actin mRNA localization in determining cell polarity and directional motility," Proceedings of the National Academy of Sciences, Jun. 19, 2001, 98(13):7045-7050.
Shi et al., "YTHDF3 facilitates translation and decay of N 6-methyladenosine-modified RNA," Cell research, Mar. 2017, 27(3):315-328.
Shin et al., "Live-cell imaging of Pol II promoter activity to monitor gene expression with RNA IMAGEtag reporters," Nucleic acids research, Jun. 17, 2014, 42(11):e90, 9 Pages.
Sikkema, "An Fc-binding protein," Amer. Biotech. Lab., Apr. 1, 1989, 7:42, 1 page.
Singh et al., "LNA (locked nucleic acids): synthesis and high-affinity nucleic acid recognition," Chemical communications, 1998, (4):455-456.
Sjoquist et al., "Protein A isolated from *Staphylococcus aureus* after digestion with lysostaphin," Eur. J. Biochem., 1972, 29:572-578.
Skuse et al., "The neurofibromatosis type I messenger RNA undergoes base-modification RNA editing," Nucleic acids research, Feb. 1, 1996, 24(3):478-486.
Soukarieh et al., "Design of nucleotide-mimetic and non-nucleotide inhibitors of the translation initiation factor eIF4E: Synthesis, structural and functional characterisation," European journal of medicinal chemistry, Nov. 29, 2016, 124:200-217.
Staals et al., "RNA targeting by the type III-A CRISPR-Cas Csm complex of Thermus thermophilus," Molecular cell, Nov. 20, 2014, 56(4):518-530.
Stepto et al., "Modelling C9ORF72 hexanucleotide repeat expansion in amyotrophic lateral sclerosis and frontotemporal dementia," Acta Neuropathol., 2014, 127(3):377-89.
Sternberg et al., "DNA interrogation by the CRISPR RNA-guided endonuclease Cas9," Nature, Mar. 2014, 507(7490): 17 Pages.
Strack et al., "A superfolding Spinach2 reveals the dynamic nature of trinucleotide repeat-containing RNA," Nature methods, Dec. 2013, 10(12): 9 Pages.
Strenkowska et al., "Cap analogs modified with 1, 2-dithiodiphosphate moiety protect mRNA from decapping and enhance its translational potential. Nucleic acids research," Nov. 16, 2016, 44(20):9578-9590.
Sunbul et al., "Contact-Mediated Quenching for RNA Imaging in Bacteria with a Fluorophore-Binding Aptamer," Angewandte Chemie International Edition, Dec. 9, 2013, 52(50), 13401-13404.
Supplementary Partial European Search Report in European Appln. No. 19788702.9, dated Jun. 11, 2021, 12 pages.
Swiech et al., "In vivo interrogation of gene function in the mammalian brain using CRISPR-Cas9," Nature biotechnology, Jan. 2015, 3(1): 9 Pages.
Tourriere et al., "The RasGAP-associated endoribonuclease G3BP assembles stress granules," The Journal of cell biology, Mar. 17, 2003, 160(6):823-831.
Tyagi et al., "Molecular beacons: probes that fluoresce upon hybridization," Nature biotechnology, Mar. 1996, 14(3):303-308.
Unsworth et al., "mRNA escape from stress granule sequestration is dictated by localization to the endoplasmic reticulum," The FASEB journal, Sep. 2010, 24(9):3370-3380.
Urnov et al., "Genome editing with engineered zinc finger nucleases," Nature Reviews Genetics, Sep. 2010, 11(9):636-646.
Vu et al., "C-to-U editing and site-directed RNA editing for the correction of genetic mutations," Bioscience trends, Jun. 30, 2017, 11(3):243-253.
Wahlestedt et al., "Potent and nontoxic antisense oligonucleotides containing locked nucleic acids," Proceedings of the National Academy of Sciences, May 9, 2000, 97(10):5633-5638.
Walczak et al., "A novel route for preparing 5' cap mimics and capped RNAs: phosphate-modified cap analogues obtained via click chemistry," Chemical science, 2017, 8(1):260-267.
Wang et al., "Crystal structure of a Pumilio homology domain," Molecular cell, Apr. 1, 2001, 7(4):855-865.
Wang et al., "Cyclohexene nucleic acids (CeNA): serum stable oligonucleotides that activate RNase H and increase duplex stability with complementary RNA," Journal of the American Chemical Society, Sep. 13, 2000, 122(36):8595-8602.
Wang et al., "Engineering splicing factors with designed specificities," Nat Methods, Nov. 2009, 6(11):825-830.
Wang et al., "Modular recognition of RNA by a human pumilio-homology domain," Cell, Aug. 23, 2002, 110(4):501-512.
Wang et al., "Probing RNA recognition by human ADAR2 using a high-throughput mutagenesis method," Nucleic acids research, Nov. 2016, 44(20):9872-9880.
Wang et al., "Unbiased detection of off-target cleavage by CRISPR-Cas9 and TALENs using integrase-defective lentiviral vectors," Nature biotechnology, Feb. 2015, 33(2): 5 Pages.
Warda et al., "Human METTL16 is a N6-methyladenosine (m6A) methyltransferase that targets pre-mRNAs and various non-coding RNAs," EMBO reports, Nov. 2017, 18(11):2004-2014.

(56) References Cited

OTHER PUBLICATIONS

Warren et al., "Highly efficient reprogramming to pluripotency and directed differentiation of human cells with synthetic modified mRNA," Cell stem cell, Nov. 5, 2010, 7(5):618-630.
Wernersson et al., "OligoWiz 2.0—integrating sequence feature annotation into the design of microarray probes," Nucleic acids research, Jul. 1, 2005, 33(suppl_2):W611-615.
Weyn-Van Hentenryci et al., "HITS-CLIP and integrative modeling define the Rbfox splicing—regulatory network linked to brain development and autism," Cell Rep., Mar. 27, 2014, 6(6): 1139-1152.
Wiedenheft et al., "RNA-guided genetic silencing systems in bacteria and archaea," Nature, Feb. 2012, 482(7385):331-338.
Wilson et al., "The structure of an antigenic determinant in a protein," Cell, 1984, 37:767-778.
Wojciechowska et al., "Cellular toxicity of expanded RNA repeats: focus on RNA foci," Human Molecular Genetics, 2011, 20:3811-3821.
Wold and Toth, "Adenovirus Vectors for Gene Therapy, Vaccination and Cancer Gene Therapy," Curr. Gene. Ther., 2013, 13(6):421-433.
Wright et al., "Biology and Applications of CRISPR Systems: Harnessing Nature's Toolbox for Genome Engineering," Cell, 2016, 164(1-2):29-44.
Wright et al., "Rational design of a split-Cas9 enzyme complex," Proceedings of the National Academy of Sciences, Mar. 10, 2015, 112(10):2984-2989.
Wu et al., "Target specificity of the CRISPRCas9 system," Quant Biol. 2014, 2(2):59-70.
Xiao et al., "Functionality and substrate specificity of human box H/ACA guide RNAs," Rna, Jan. 1, 2009, 15(1):176-186.
Xiao et al., "Nuclear m6A reader YTHDC1 regulates mRNA splicing," Molecular cell, Feb. 18, 2016, 61(4):507-519.
Xu et al., "A CRISPR—dCas toolbox for genetic engineering and synthetic biology," Journal of molecular biology, Jan. 4, 2019, 431(1):34-47.
Yamanaka et al., "A novel translational repressor mRNA is edited extensively in livers containing tumors caused by the transgene expression of the apoB mRNA-editing enzyme," Genes & development, Feb. 1, 1997, 11(3):321-333.
Yan et al., "Cas13d is a compact RNA-targeting type VI CRISPR effector positively modulated by a WYL-domain-containing accessory protein," Molecular cell, Apr. 19, 2018 70(2):327-339.
Yang et al., "Effective gene targeting in rabbits using RNA-guided Cas9 nucleases," Journal of molecular cell biology, Feb. 1, 2014, 6(1):97-99.
Yeo. et al., "An RNA code for the FOX2 splicing regulator revealed by mapping RNA-protein interactions in stem cells," Nature structural & molecular biology, Feb. 2009, 16(2): 130-137.
Ying et al., "Cancer therapy using a self-replicating RNA vaccine," Nat. Med., 1999, 5(7):823-827.
Zaganelli et al., "The pseudouridine synthase RPUSD4 is an essential component of mitochondrial RNA granules," Journal of Biological Chemistry, Mar. 17, 2017, 292(11):4519-4532.
Zambrowicz et al., "Disruption of overlapping transcripts in the ROSA beta geo 26 gene trap strain leads to widespread expression of beta-galactosidase in mouse embryos and hematopoietic cells," Proc. Natl. Acad. Sci., 1997, 94:3789-3794.
Zetche et al., "A split-Cas9 architecture for inducible genome editing and transcription modulation," Nat Biotechnol., 2015, 33(2): 6 Pages.
Zetsche et al., "A split-Cas9 architecture for inducible genome editing and transcription modulation," Nature biotechnology, Feb. 2015, 33(2): 3 Pages.
Zhang et al., "Treatment of type 1 myotonic dystrophy by engineering site-specific RNA endonuleases that target (CUG)(n)," Molecular Therapy, Feb. 1, 2014, 22(2):312-320.
Zuris et al., "Efficient Delivery of Genome-Editing Proteins in vitro and in vivo," Nature Biotechnol., Jan. 2015, 33(1): 26 Pages.
GenBank Accession No. NP 001124150.1, "eukaryotic translation initiation factor 4E isoform 3 [*Homo sapiens*]," Sep. 3, 2019, 3 pages.
Hinnebusch, "Molecular Mechanism of Scanning and Start Codon Selection in Eukaryotes," Microbiology and Molecular Biology Reviews, Sep. 2011, 75(3):434-467.
International Preliminary Report on Patentability in International Appln. No. PCT/US2016/063429, dated May 29, 2018, 12 pages.
International Search Report and Written Opinion in International Appln. No. PCT/US2020/028501, dated Sep. 25, 2020, 12 pages.
International Search Report and Written Opinion in International Appln. No. PCT/US2020/028546, dated Jul. 14, 2020, 13 pages.
Cong et al., "In Vivo Genome Engineering With AAV Vector Carrying CRISPR-Cas9 System," InMolecular Therapy, May 1, 2014, 22(1): S214, Abstract 551.
Cowling, "Regulation of mRNA cap methylation," Biochemical Journal, Jan. 15, 2010, 425(2):295-302.
Faure et al., "Comparative genomics and evolution of trans-activating RNAs in Class 2 CRISPR-Cas systems," RNA Biology, Apr. 3, 2019, 16(4):435-448.
He et al., "Conjugation and Evaluation of Triazole-Linked Single Guide RNA for CRISPR-Cas9 Gene Editing," ChemBioChem, Oct. 4, 2016, 17(19):1809-1812.
Jiang et al., "CRISPR-Cas9 structures and mechanisms," Annual Review of Biophysics, May 22, 2017, 46(1):505-529.
Mu et al., "5' capped and 3' polyA-tailed sgRNAs enhance the efficiency of CRISPR-Cas9 system," Protein & Cell, Mar. 2019, 10(3):223-228.
Noack et al., "Epitranscriptomics: a new regulatory mechanism of brain development and function," Frontiers in Neuroscience, Feb. 20, 2018, 12(85):1-9.
Wolter et al., "The CRISPR/Cas revolution reaches the RNA world: Cas13, a new Swiss Army knife for plant biologists," The Plant Journal, Jun. 2018, 94(5):767-775.
Extended European Search Report in EP Appln. No. 22195456.3, dated Mar. 14, 2023, 11 pages.
Ramanathan et al., "mRNA capping: biological functions and applications," Nucleic Acids Research, Sep. 19, 2016, 44(16):7511-7526.
Glavan et al., "Structures of the PIN domains of SMG6 and SMG5 reveal a nuclease within the mRNA surveillance complex," The EMBO Journal, Nov. 1, 2006, 25(21):5117-5125.
Nishimasu, "Crystal Structure of Cas9," Journal of the Crystallographic Society of Japan, Apr. 30, 2015, 57(2):96-103 (with English abstract).
Adachi et al., "Targeted pseudouridylation: an approach for suppressing nonsense mutations in disease genes," Molecular Cell, Feb. 16, 2023, 83(4):637-651.
Koeppen, "The pathogenesis of spinocerebellar ataxia," The Cerebellum, Mar. 2005, 4:62-73.
Raz et al., "191st ENMC international workshop: recent advances in oculopharyngeal muscular dystrophy research: from bench to bedside Jun. 8-10, 2012, Naarden, The Netherlands," Neuromuscular Disorders, Jun. 2013, 23(6):516-523.
Wee et al., "The genetics of spinal muscular atrophies," Current Opinion in Neurology, Oct. 2010, 23(5):450-458.

* cited by examiner

PROTEIN TRANSLATIONAL CONTROL

CROSS-REFERENCE TO RELATED APPLICATIONS

This application is a National Stage Application under 35 U.S.C. § 371 and claims the benefit of International Application No. PCT/US2020/028501, filed Apr. 16, 2020, which claims priority to U.S. Patent Application Ser. No. 62/834,582, filed Apr. 16, 2019. The entire contents of the foregoing are incorporated herein by reference in its entirety.

STATEMENT OF GOVERNMENT SUPPORT

This invention was made with government support under EY029166 and NS103172, awarded by the National Institutes of Health. The government has certain rights in the invention.

BACKGROUND

There exist many methods for downregulating gene expression, including siRNA, miRNA, and anti-sense approaches. Existing methods for enhancing gene expression, such as delivery of mRNAs can be inefficient and technically challenging. Accordingly, there is a need to develop novel approaches for enhancing protein translation.

SUMMARY

In one aspect, provided herein is a cap-conjugated oligonucleotide comprising an m7G cap or a variant or analog thereof conjugated to an oligonucleotide, wherein the oligonucleotide is capable of specifically hybridizing with a target sequence in an RNA molecule. In some embodiments, the RNA molecule is a messenger RNA (mRNA). In some embodiments, the mRNA has an endogenous m7G cap. In some embodiments, the target sequence is downstream of the endogenous m7G cap of the mRNA. In some embodiments, the mRNA comprises a start codon, and wherein the 5' end of the target sequence is upstream of the start codon. In some embodiments, the 5' end of the target sequence is between 1 and 50 nucleotides upstream of the first nucleotide of the start codon. In some embodiments, the target sequence comprises the start codon. In some embodiments, the mRNA comprises a start codon, and wherein the 5' end of the target sequence is downstream of the start codon. In some embodiments, the 5' end of the target sequence is between 1 and 50 nucleotides downstream of the last nucleotide of the start codon. In some embodiments, the oligonucleotide is at least 80% complementary to the target sequence. In some embodiments, the oligonucleotide is at least 90% complementary to the target sequence. In some embodiments, the oligonucleotide comprises about 5 to about 30 nucleotides. In some embodiments, the oligonucleotide comprises one or more backbone modifications. In some embodiments, the oligonucleotide comprises one or more phosphorothioate linkages. In some embodiments, the oligonucleotide comprises one or more locked nucleic acids (LNAs). In some embodiments, the oligonucleotide comprises 5 to 15 LNAs. In some embodiments, the 5 to 15 LNAs are consecutive. In some embodiments, the oligonucleotide comprises one or more substituted sugar moieties. In some embodiments, the oligonucleotide comprises one or more nucleotides modified at the 2' position of the sugar. In some embodiments, the one or more nucleotides comprise a 2' O-methyl. In some embodiments, the one or more nucleotides comprise 2'-O-methoxyethyl. In some embodiments, the oligonucleotide comprises 10 to 25 nucleotides having a 2' O-methyl. In some embodiments, the oligonucleotide comprises fewer than 25 nucleotides. In some embodiments, the oligonucleotide comprises one or more LNAs and one or more nucleotides having a 2' O-methyl. In some embodiments, the oligonucleotide comprises one or more LNAs and one or more nucleotides having a 2'-O-methoxyethyl. In some embodiments, the m7G cap or a variant or analog thereof comprises a structure of

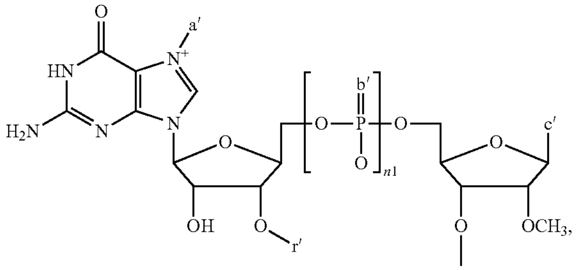

wherein a' is methyl or a functional group configured to enhance association with an EIF4E protein, r' is methyl or a functional group configured to prevent further extension, b' is oxygen, sulfur, or boron, c' is a nitrogenous base, and n1 is equal to or fewer than 4. In some embodiments, a' is (4-Chlorophenyl-ethyl)- or (4-Fluorophenyl-ethyl)-. In some embodiments, r' is —O-Methyl. In some embodiments, c' is an adenine, guanine, cytosine, thymine, or uracil. In some embodiments, the m7G cap or a variant or analog thereof comprises a structure of

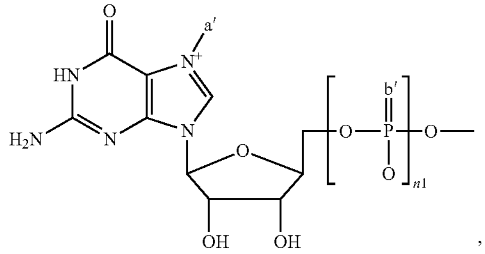

, wherein a' is methyl or a functional group configured to enhance association with an EIF4E protein, b' is oxygen, sulfur, or boron, and n1 is equal to or fewer than 4. In some embodiments, a' is (4-Chlorophenyl-ethyl)- or (4-Fluorophenyl-ethyl)-. In some embodiments, the m7G cap or a variant or analog thereof is conjugated to the oligonucleotide via a linker. In some embodiments, the linker is a polymeric linker. In some embodiments, the linker is polyethylene glycol (PEG). In some embodiments, the linker comprises 2 to 30 PEG subunits. In some embodiments, the m7G cap or a variant or analog thereof is conjugated to the 5' end of the oligonucleotide. In some embodiments, the m7G cap or a variant or analog thereof is conjugated to the 3' end of the oligonucleotide. In some embodiments, the m7G cap or a variant or analog thereof is conjugated to a nucleotide between the 5' end and the 3' end of the oligonucleotide. In some embodiments, two or more m7G caps or a variant or analog thereof are conjugated to the oligonucleotide. In some aspects, provided herein are pharmaceutical compositions comprising any of the cap-conjugated oligonucleotides described herein and a pharmaceutically acceptable carrier.

In another aspect, provided herein is a method of regulating translation of an mRNA in a cell, the methods comprise contacting the cell with a cap-conjugated oligonucleotide comprising an m7G cap or a variant or analog thereof conjugated to an oligonucleotide, wherein the oligonucleotide comprises a sequence capable of specifically hybridizing with a target sequence in an RNA molecule. In some embodiments, the RNA molecule is an mRNA. In some embodiments, the mRNA has an endogenous m7G cap. In some embodiments, the target sequence is downstream of the endogenous m7G cap of the mRNA. In some embodiments, the mRNA comprises a start codon, and wherein the 5' end of the target sequence is upstream of the start codon. In some embodiments, the 5' end of the target sequence is between 1 and 50 nucleotides upstream of the first nucleotide of the start codon. In some embodiments, the target sequence comprises the start codon. In some embodiments, the mRNA comprises a start codon, and wherein the 5' end of the target sequence is downstream of the start codon. In some embodiments, the 5' end of the target sequence is between 1 and 50 nucleotides downstream of the last nucleotide of the start codon. In some embodiments, the oligonucleotide is at least 80% complementary to the target sequence. In some embodiments, the oligonucleotide is at least 90% complementary to the target sequence. In some embodiments, the oligonucleotide comprises about 5 to about 30 nucleotides. In some embodiments, the oligonucleotide comprises one or more backbone modifications. In some embodiments, the oligonucleotide comprises one or more phosphorothioate linkages. In some embodiments, the oligonucleotide comprises one or more locked nucleic acids (LNAs). In some embodiments, the oligonucleotide comprises 5 to 15 LNAs. In some embodiments, the 5 to 15 LNAs are consecutive. In some embodiments, the oligonucleotide comprises one or more substituted sugar moieties. In some embodiments, the oligonucleotide comprises one or more nucleotides modified at the 2' position of the sugar. In some embodiments, the one or more nucleotides comprise a 2' O-methyl. In some embodiments, the one or more nucleotides comprise 2'-O-methoxyethyl. In some embodiments, the oligonucleotide comprises 10 to 25 nucleotides having a 2' O-methyl. In some embodiments, the oligonucleotide comprises fewer than 25 nucleotides. In some embodiments, the oligonucleotide comprises one or more LNAs and one or more nucleotides having a 2' O-methyl. In some embodiments, the one or more nucleotides comprise 2'-O-methoxyethyl. In some embodiments, the m7G cap or a variant or analog thereof comprises a structure of

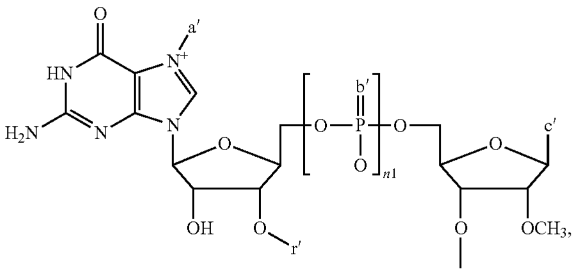

wherein a' is methyl or a functional group configured to enhance association with an EIF4E protein, r' is methyl or a functional group configured to prevent further extension, b' is oxygen, sulfur or boron, c' is a nitrogenous base, and n1 is equal to or fewer than 4. In some embodiments, a' is (4-Chlorophenyl-ethyl)- or (4-Fluorophenyl-ethyl)-. In some embodiments, r' is —O-Methyl. In some embodiments, c' is an adenine, guanine, cytosine, thymine, or uracil. In some embodiments, the m7G cap or a variant or analog thereof comprises a structure of

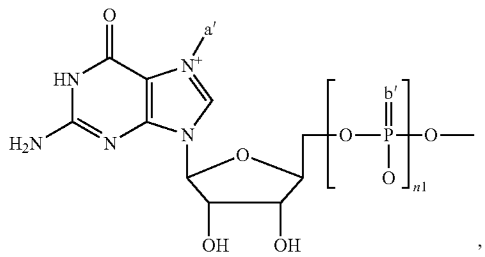

wherein a' is methyl or a functional group configured to enhance association with an EIF4E protein, b' is oxygen, sulfur or boron, and n1 is equal to or fewer than 4. In some embodiments, a' is (4-Chlorophenyl-ethyl)- or (4-Fluorophenyl-ethyl)-. In some embodiments, the m7G cap or a variant or analog thereof is conjugated to the oligonucleotide via a linker. In some embodiments, the linker is a polymeric linker. In some embodiments, the linker is polyethylene glycol (PEG). In some embodiments, the linker comprises 2 to 30 PEG subunits. In some embodiments, the m7G cap or a variant or analog thereof is conjugated to the 5' end of the oligonucleotide. In some embodiments, the m7G cap or a variant or analog thereof is conjugated to the 3' end of the oligonucleotide. In some embodiments, the m7G cap or a variant or analog thereof is conjugated to a nucleotide between the 5' end and the 3' end of the oligonucleotide. In some embodiments, two or more m7G caps or a variant or analog thereof are conjugated to the oligonucleotide.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated. All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications, patents, and patent applications incorporated by reference contradict the disclosure contained in the specification, the specification is intended to supersede and/or take precedence over any such contradictory material.

DESCRIPTION OF THE DRAWINGS

FIG. 1A is a schematic showing an exemplary location for the hybridization sites in the BRCA1 transcript. FIG. 1B shows BRCA1 protein expression levels upon treatment with oligonucleotides not conjugated with an m7G cap. FIG. 1C shows BRCA1 protein expression levels upon treatment with m7G cap-conjugated oligonucleotides.

DETAILED DESCRIPTION

Figure 1A:
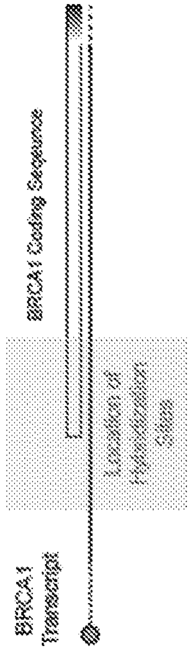
FIGS. 1A-1C show BRCA1 translational control using m7G cap-conjugated oligonucleotide.

The vast majority of gene regulatory drugs have been designed to knockdown gene expression (i.e., siRNAs, miRNAs, anti-sense, etc.). Some methods exist to enhance gene expression, such as the delivery of mRNAs; however, therapeutic delivery of such large and charged RNA molecules is technically challenging, inefficient, not particularly practical and can be highly immunogenic. Classical gene therapy approaches involve delivery of a gene product as viral-encoded products (e.g., AAV or lentivirus-packaged products); however, these methods suffer from not being able to accurately reproduce the correct alternatively spliced isoforms in the correct ratios. Additional methods of regulating protein translation include those utilizing engineered RNA binding proteins. One such engineered RNA binding protein repurposes the binding activity of PUF family of proteins, which recognize RNA sequences at single base resolution. PUF proteins can be fused to translation initiation factors (e.g., EIF4G) to promote protein production. However, engineered RNA binding proteins require extensive engineering for each target RNA sequence, and in the case of PUF proteins, cannot recognize cytosine RNA bases thus limiting their applicability. PUF protein fusions are also large and have exhibited high affinities for target RNA sites, which may confine their use to specific mRNA regions (e.g., the 3'UTR, where helicase activity and ribosome translocation are largely absent). More problematic with this methodology is the act of expression itself, whereby the introduction of PUF/translation initiation factor fusion proteins likely disrupts the stoichiometry of translation machinery maintained by the cell.

The most widely accepted view on translation initiation in mammalian cells starts with the binding of the 5' methyl-7 guanosine (m7G) cap structure by Eukaryotic Initiation Factor 4E (EIF4E), which results in the nucleation of translational pre-initiation complexes on the adjacent 5' untranslated region (5'UTR) of mRNA. The bound pre-initiation complexes then scan the 5'UTR unidirectionally (5' to 3') for suitable start codons (e.g., “AUG”) to prime and initiate translation. The 5' m7G cap is an evolutionarily conserved modification of eukaryotic mRNA, and serves as a unique molecular module that recruits cellular proteins and mediates cap-related biological functions such as pre-mRNA processing, nuclear export, and cap-dependent protein synthesis.

Provided herein are compositions and methods for enhancing protein production by recruiting an m7G cap to an mRNA using cap-conjugated oligonucleotides.

In some aspects, provided herein are cap-conjugated oligonucleotides comprising an m7G cap or an analog thereof conjugated to an oligonucleotide, wherein the oligonucleotide is capable of specifically hybridizing with a target sequence in an RNA molecule (e.g., an mRNA).

In some embodiments, upon hybridization between the oligonucleotide and the target sequence, the m7G cap associated with the oligonucleotide is brought closer to a desired start codon in the target mRNA as compared to the endogenous m7G cap of the target mRNA. Also provided are methods of regulating translation of an mRNA in a cell, the method comprising contacting the cell with a cap-conjugated oligonucleotide comprising an m7G cap or an analog thereof conjugated to an oligonucleotide, wherein the oligonucleotide comprises a sequence capable of specifically hybridizing with a target sequence in an RNA molecule.

Each strand of DNA or RNA has a 5' end and a 3' end, corresponding to the carbon position on the deoxyribose (or ribose) ring. “Upstream” as described herein can mean toward the 5' end of an RNA molecule and “downstream” as described herein can mean towards the 3' end of an RNA molecule. A “start codon” as described herein can refer to the first codon of an open reading frame on a messenger RNA transcript translated by a ribosome. The most common start codon is AUG. Alternative start codons from both prokaryotes and eukaryotes such as, but not limited to, GUG, UUG, AUU, and CUG are also provided.

As used in the description of the invention and the appended claims, the singular forms “a,” “an” and “the” are intended to include the plural forms as well, unless the context clearly indicates otherwise.

The term “about,” as used herein when referring to a measurable value such as an amount or concentration and the like, is meant to encompass variations of 20%, 10%, 5%, 1%, 0.5%, or even 0.1% of the specified amount.

The terms “acceptable,” “effective,” “efficient” or “sufficient” when used to describe the selection of any components, ranges, dose forms, etc. disclosed herein intend that said component, range, dose form, etc. is suitable for the disclosed purpose.

Also as used herein, “and/or” refers to and encompasses any and all possible combinations of one or more of the associated listed items, as well as the lack of combinations when interpreted in the alternative (“or”).

As used herein, the term “comprising” is intended to mean that the compositions and methods include the recited elements, but do not exclude others. As used herein, the transitional phrase “consisting essentially of” (and grammatical variants) is to be interpreted as encompassing the recited materials or steps and those that do not materially affect the basic and novel characteristic(s) of the recited embodiment. Thus, the term “consisting essentially of” as used herein should not be interpreted as equivalent to “comprising.” “Consisting of” shall mean excluding more than trace elements of other ingredients and substantial method steps for administering the compositions disclosed herein. Aspects defined by each of these transition terms are within the scope of the present disclosure.

As used herein, the term “functional” may be used to modify any molecule, biological, or cellular material to intend that it accomplishes a particular, specified effect.

The term “target sequence” can refer to a nucleic acid sequence present in an RNA molecule to which a cap-conjugated oligonucleotide can hybridize, provided sufficient conditions for hybridization exist. Hybridization between the cap-conjugated oligonucleotide and the target sequence can, for example, be based on Watson-Crick base pairing rules, which enables programmability in the oligonucleotide sequence. The oligonucleotide sequence can be designed, for instance, to hybridize with any target sequence.

"Binding" as used herein can refer to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it means that the molecule X binds to molecule Y in a non-covalent manner). Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. Kd is dependent on environmental conditions, e.g., pH and temperature, as is known by those in the art. "Affinity" can refer to the strength of binding, and increased binding affinity is correlated with a lower Kd.

The terms "hybridizing" or "hybridize" can refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences or segments of sequences are "substantially complementary" if at least 80% of their individual bases are complementary to one another.

As used herein, "complementary" can mean that two nucleic acid sequences have at least 50% sequence identity. Preferably, the two nucleic acid sequences have at least 60%, 70%, 80%, 90%, 95%, 96%, 97%, 98%, 99%, or 100% of sequence identity. "Complementary" also means that two nucleic acid sequences can hybridize under low, middle, and/or high stringency condition(s).

As used herein, "substantially complementary" means that two nucleic acid sequences have at least 90% sequence identity. Preferably, the two nucleic acid sequences have at least 95%, 96%, 97%, 98%, 99%, or 100% of sequence identity. "Substantially complementary" can also mean that two nucleic acid sequences can hybridize under high stringency condition(s).

Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

As used herein, "contacting" a cell with a nucleic acid molecule can be allowing the nucleic acid molecule to be in sufficient proximity with the cell such that the nucleic acid molecule can be introduced into the cell.

"Nucleic acids" may be naturally occurring nucleic acids such as DNA and RNA, or artificial nucleic acids including peptide nucleic acid (PNA), morpholino, locked nucleic acid (LNA), glycol nucleic acid (GNA), and threose nucleic acid (TNA). Both single-stranded and double-stranded nucleic acids are included.

As used herein, "conjugate" can refer to linking or connecting two or more molecules, such as nucleic acids, via a covalent link.

The term "cell" as used herein may refer to either a prokaryotic or eukaryotic cell, optionally obtained from a subject or a commercially available source.

The term "encode" as it is applied to nucleic acid sequences refers to a polynucleotide which is said to "encode" a polypeptide, an mRNA, or an effector RNA if, in its native state or when manipulated by methods well known to those skilled in the art, can be transcribed and/or translated to produce the effector RNA, the mRNA, or an mRNA that can for the polypeptide and/or a fragment thereof. The antisense strand is the complement of such a nucleic acid, and the encoding sequence can be deduced therefrom.

As used herein, the term "expression" or "gene expression" refers to the process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample.

As used herein, "contacting" a cell with a nucleic acid molecule can include allowing the nucleic acid molecule to be in sufficient proximity with the cell such that the nucleic acid molecule can be introduced into the cell.

A "promoter" can be a region of DNA that leads to initiation of transcription of a gene.

I. m7G Cap

An m7G cap, or 7-methylguanosine cap, includes a guanine nucleotide methylated on the 7 position. In eukaryotes, m7G caps can be found on the 5' end of an mRNA molecule, which is connected with the mRNA via a 5' to 5' triphosphate linkage. m7G caps disclosed herein can further include a second nucleotide, which is linked to the guanine nucleotide via 1, 2, 3, or 4 phosphate groups, referred to as the di-nucleotide m7G cap. The second nucleotide can be an adenosine, guanosine, cytidine, thymidine, or uridine, and can be 2'-O-methylated.

Variants of the m7G cap can include modifications at various positions. For example, the 7 position of the guanine nucleotide can be a functional group other than a methyl that can enhance EIF4E association (e.g. (4-Chlorophenyl-ethyl)-; (4-Fluorophenyl-ethyl)-; See Cai et al. (1999) Biochemistry, 38: 8538-8547, Chen et al. (2012) Journal of Medicinal Chemistry, 55:3837-3851, Soukarieh et al. (2016) European Journal of Medicinal Chemistry, 124: 200-217). The 3' hydroxyl group in the guanine nucleotide can be methylated to prevent further conjugation. The 3' hydroxyl group can also be substituted with other functional groups to prevent further conjugation (e.g. —O-Methyl). The phosphodiester bonds in the phosphate groups of di-nucleotide caps can be substituted with phosphorothioate bonds. In some instances, the m7G cap or variants thereof have the following structure (Structure A):

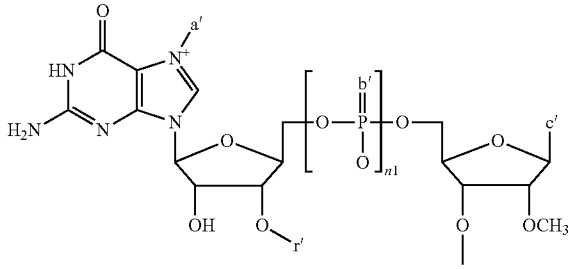

where a' can be methyl or a functional group configured to enhance association with an EIF4E protein (e.g. (4-Chlorophenyl-ethyl)-; (4-Fluorophenyl-ethyl)-), r' can be methyl or a functional group configured to prevent further extension (e.g. —O-Methyl), b' can be oxygen, sulfur or boron, c' can be a nitrogenous base (e.g., adenine, guanine, cytosine, thymine, or uracil), and n1 can be equal to or fewer than 4. In some instances, the m7G cap or variants thereof have the following structure (Structure B):

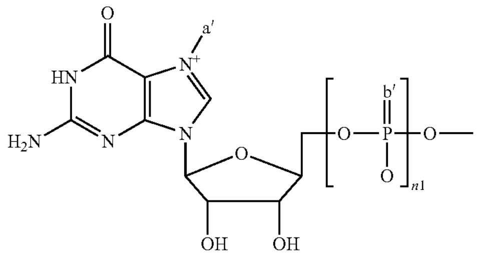

where a' can be methyl or a functional group configured to enhance association with an EIF4E protein e.g. (4-Chlorophenyl-ethyl)-; (4-Fluorophenyl-ethyl)), b' can be oxygen, sulfur or boron, and n1 can be equal to or fewer than 4.

Also contemplated herein are analogs of the m7G cap. For example, standard cap analog m7G(5')pppG can be conjugated to the oligonucleotide of the present disclosure and simulate the m7G cap structure. Standard cap analogs can be conjugated to the oligonucleotide in the forward (e.g., [m7G (5')pppG(pN)]) or the reverse orientation (e.g., [G(5') pppm7G(pN)]). The cap analog ARCA (anti-reverse cap analog), where one of the 3' OH groups is eliminated from the cap analog and is substituted with —$OCH_3$. An exemplary structure of ARCA (m7(3'-O-methyl)-G(5')ppp(5')G) is shown below (Structure C):

Additional cap analogs contemplated herein also include unmethylated cap analogs (e.g., GpppG), trimethylated cap analogs (e.g., $m_3^{2.2.7}GP_3G$), and $m_2^{7,3'-O}GP_3$(2'OMe)ApG.

The m7G cap and variants and analogs thereof as disclosed herein may include chemical modifications relative to the naturally occurring m7G cap. For example, chemical modifications that can reduce the sensitivity of the m7G cap to cellular decapping enzymes are useful for the present disclosure. Chemical modifications at either the 2' or 3' OH group are contemplated. Suitable chemical modifications include those with 1,2-dithiodiphosphate (See, e.g. Strenkowska et al., Nucleic Acids Res. 44(20):9578-9590 (2016)), phosphate-modified cap analogues (e.g. those described in Walczak et al., Chem Sci. 8(1):260-267 (2017)), as well as those described in Basolo et al., Eur J Endocrinol., 145(5):599-604 (2001), and Borghardt et al., Can Respir J. 2018 Jun. 19; 2018: 2732017.

II. Cap-Conjugated Oligonucleotides

The present disclosure provides cap-conjugated oligonucleotides comprising an m7G cap or a variant or analog thereof conjugated to an oligonucleotide, wherein the oligonucleotide is capable of specifically hybridizing with a target sequence in an RNA molecule (e.g., an mRNA).

The mRNA can include an endogenous m7G cap, and the target sequence can be downstream of the endogenous m7G cap. The mRNA can include one or more start codons, and any one of the one or more start codons can be chosen as the desired start codon. The 5' end of the target sequence can either be upstream of the first nucleotide of the desired start codon, or downstream of the last nucleotide of the desired start codon. The 5' end of the target sequence can be located between 1 to 50 nucleotides (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides) upstream of the first nucleotide of the desired start codon. In some instances, the target sequence encompasses the desired start codon. The 5' end of the target sequence can alternatively be located between 1 to 50 nucleotides (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides) downstream of the last nucleotide in the desired start codon.

The oligonucleotide is capable of hybridizing with a target sequence in an RNA (e.g., an mRNA). The oligonucleotide can include a sequence that is at least 80% (e.g., at least 81%, 82%, 83%, 84%, 85%, 86%, 87%, 88%, 89%, 90%, 91%, 92%, 93%, 94%, 95%, 96%, 97%, 98%, or 99%) complementary to the target sequence. The oligonucleotide can include 5 to 30 nucleotides (e.g. 8 to 27, 11 to 24, 14 to 21, or 16 to 19 nucleotides).

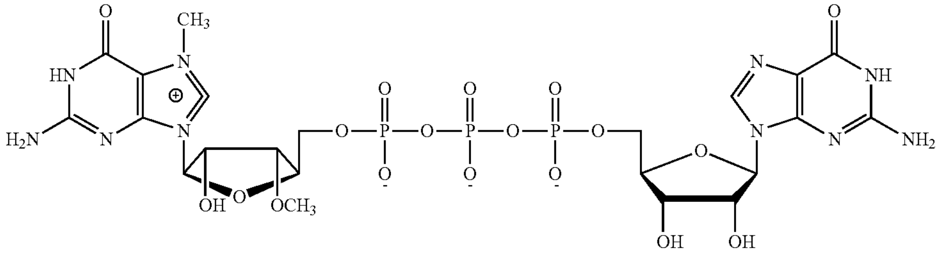

Upon hybridization between the cap-conjugated oligonucleotide and the target sequence, the m7G cap or a variant or analog thereof in the cap-conjugated oligonucleotide can be recruited to the vicinity of the desired start codon, and closer in proximity to the desired start codon than the endogenous m7G cap of the mRNA. The m7G cap or a variant or analog thereof of the bound cap-conjugated oligonucleotide can subsequently recruit translation initiation factors (e.g., EIF4E) and initiate protein translation from the desired start codon. Such recruitment of the translation initiation factors to a start codon via a cap-conjugated oligonucleotide can enhance protein translation, as compared to protein translation initiated by the endogenous m7G cap of the mRNA.

An exemplary structure (Structure D) of the cap-conjugated oligonucleotide is shown below:

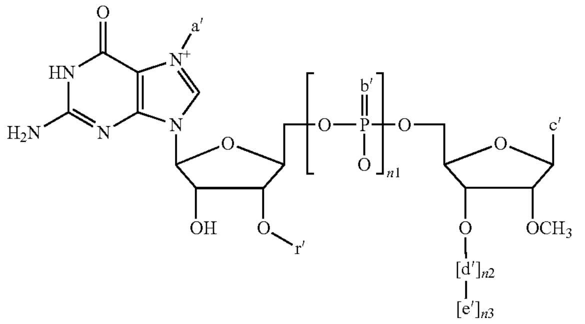

where a' can be methyl or a functional group configured to enhance association with an EIF4E protein (e.g. 4-Chlorophenyl-ethyl)-; (4-Fluorophenyl-ethyl)-), r' can be methyl or a functional group configured to prevent further extension (e.g. —O-Methyl), b' can be oxygen, sulfur, or boron, c' can be a nitrogenous base (e.g. adenine, guanine, cytosine, thymine or uracil), and n1 can be equal to or fewer than 4. Additionally, d' can be a linker of variable length (e.g., a polymeric linker (e.g. a biocompatible polymeric linker, such as PEG)), and e' can be an oligonucleotide capable of hybridizing with a target sequence in an RNA (e.g., mRNA). n2 can be between 2 and 30 units and n3 can be between 5 and 25 units. e' can include modifications that reduce sensitivity to cellular nucleases and increase overall stability, such as locked nucleic acid (LNA), 2'-modifications, and phosphorothioate backbone modifications. For example, e' can include (2'O-methyl) nucleic acids (10<n3<25 units), LNAs (5<n3<15 units), or an intermediate combination of both (n3<25 units). As shown in Structure D, the m7G cap or a variant or analog thereof is conjugated to e' via a linker d'. However, the m7G cap or a variant or analog thereof can be conjugated to e' at either the 5' end, the 3' end, or at any nucleotides between the 5' and 3' ends. In some embodiments, two or more (e.g., 2, 3, 4, or 5) m7G caps are conjugated to the same oligonucleotide. In some embodiments, two m7G caps are conjugated to the same oligonucleotide, with one on the 5' end and the other on the 3' end.

Another exemplary structure (Structure E) of the cap-conjugated oligonucleotide is shown below:

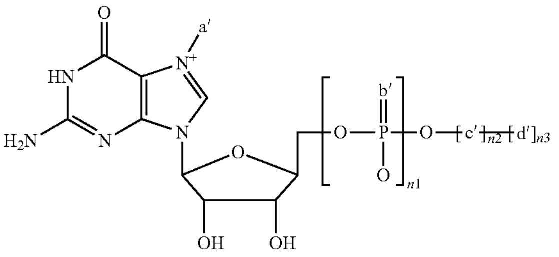

where a' can be methyl or a functional group configured to enhance association with an EIF4E protein, b' can be oxygen, sulfur or boron, and n1 can be equal to or fewer than 4. c' can be a linker of variable length (e.g., a polymeric linker (e.g. a biocompatible polymeric linker, such as PEG)), and d' can be an oligonucleotide capable of hybridizing with a target sequence in an RNA (e.g., mRNA). n2 can be between 2 and 30 units and n3 can be between 5 and 25 units. d' can include modifications that reduce sensitivity to cellular nucleases and increase overall stability, such as locked nucleic acid (LNA), 2'-modifications, and phosphorothioate backbone modifications. For example, e' can include (2'O-methyl) nucleic acids (10<n3<25 units), LNAs (5<n3<15 units), or an intermediate combination of both (n3<25 units). As shown in Structure E, the m7G cap or a variant or analog thereof is conjugated to d' via a linker c'. However, the m7G cap or a variant or analog thereof can be conjugated to d' at either the 5' end, the 3' end, or at any nucleotides between the 5' and 3' ends.

A further exemplary structure (Structure F) of the cap-conjugated oligonucleotide is shown below:

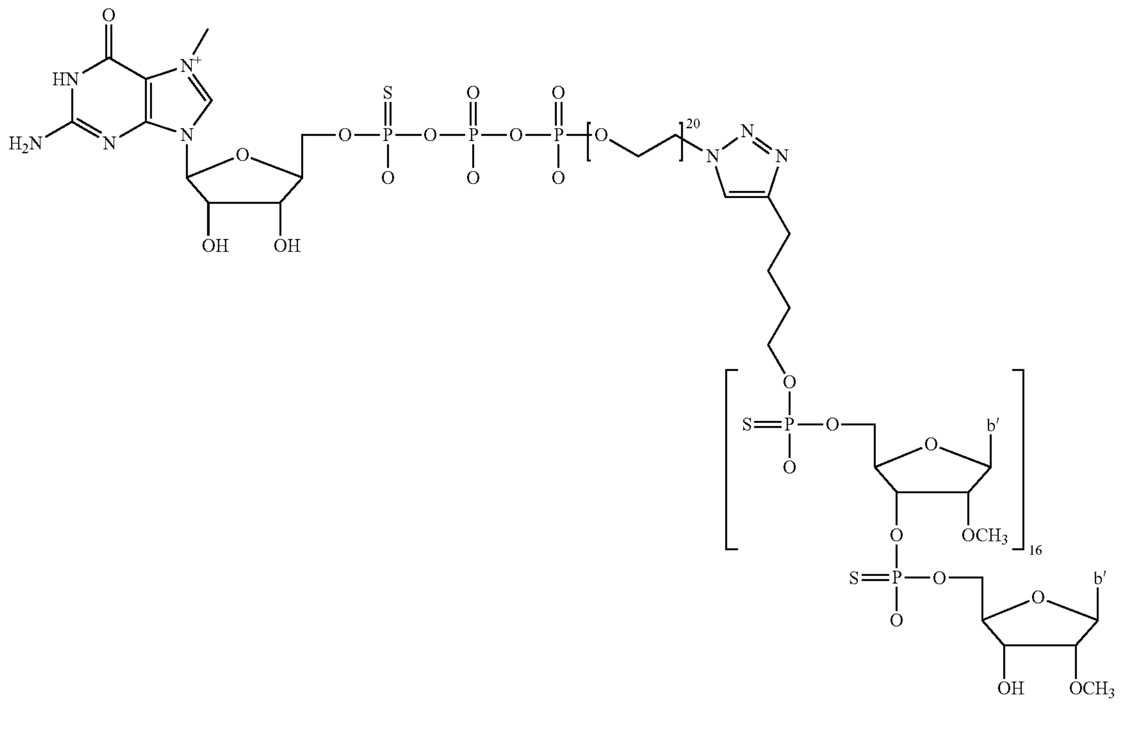

where b' can be a sequence of nitrogenous bases, e.g., adenine, guanine, cytosine, thymine, and uracil, which defines a polymer of nucleic acids that are complementary in sequence to regions of messenger RNA in close proximity to start codons.

Modifications

A cap-conjugated oligonucleotide of the present disclosure can include one or more modifications. Suitable modifications that can sequence specifically recruit a Cap analog to a target RNA molecule are contemplated herein (e.g., LNA, BNA, PNA, GNA, or morpholino nucleic acid). Suitable modifications also include those that can enhance the stability of the oligonucleotide and or affinity for a target RNA sequence. An oligonucleotide of the present disclosure can include one or more modifications in the backbone. Non-limiting examples of backbone modifications include: 2' methoxy (2'OMe), 2' fluorine (2'fluoro), 2'-O-methoxyethyl (MOE), locked nucleic acids (LNA), unlocked nucleic acids (UNA), bridged nucleic acids, 2'deoxynucleic acids (DNA), and peptide nucleic acids (PNA). Alternatively or additionally, an oligonucleotide can include at least one base modification. Non-limiting examples of base modifications include: 2-aminopurine, inosine, thymine, 2,6-diaminopurine, 2-pyrimidinone, and 5-methyl cytosine. In some instances, an RNA fragment comprises at least one phosphorothioate linkage.

Modifications in the oligonucleotides can be used to, e.g., enhance stability, reduce the likelihood or degree of innate immune response, and improve binding capacity. By way of illustration of various types of modifications, modifications can include one or more nucleotides modified at the 2' position of the sugar, such as but not limited to, a 2'-O-alkyl, 2'-O-alkyl-O-alkyl, or 2'-fluoro-modified nucleotide. DNA (2'deoxy-) nucleotide substitutions are also contemplated. Non-limiting examples of RNA modifications also include 2'-fluoro, 2'-amino, 2' O-methyl modifications on the ribose of pyrimidines, and basic residues or an inverted base at the 3' end of the RNA. Such modifications can be incorporated into oligonucleotides, and these oligonucleotides have been shown to have a higher $T_m$ (e.g., higher target binding affinity) than 2'-deoxy oligonucleotides against a given target.

An oligonucleotide according to any of the embodiments described herein can include, for example, a modification that increases resistance to nuclease digestion as compared to the native nucleic acid. In some instances, the modified nucleic acid comprises a modified backbone selected from, for example, phosphorothioates, phosphotriesters, methyl phosphonates, short chain alkyl or cycloalkyl intersugar linkages, and short chain heteroatomic or heterocyclic intersugar linkages. The nucleic acid can have a phosphorothioate backbone or a heteroatom backbone, e.g., $CH_2$—NH—O—$CH_2$, CH, —N($CH_3$)—O—$CH_2$ (known as a methylene (methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones; amide backbones (see De Mesmaeker et al. (1995) *Acc. Chem. Res.,* 28(9):366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al. (1991) *Science.* 254(5037):1497-1500). Phosphorus-containing linkages include, but are not limited to, phosphorothioates, chiral phosphorothioates, phosphorodithioates, phosphotriesters, aminoalkylphosphotriesters, methyl and other alkyl phosphonates including 3'alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see, e.g., U.S. Pat. Nos. 3,687,808; 4,469,863; 4,476,301; 5,023,243; 5,177, 196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Braasch et al. (2002) *Biochem.,* 41(14):4503-4510*; Genesis,* Volume 30, Issue 3, (2001) Wiley Online Library; Heasman (2002) *Dev. Biol.,* 243(2):209-214; Nasevicius et al. (2000) *Nat. Genet.,* 26(2):216-220; Lacerra et al. (2000) *Proc. Natl. Acad. Sci. USA.* 97(17):9591-9591; and U.S. Pat. No. 5,034,506. Cyclohexenyl nucleic acid oligonucleotide mimetics are described in Wang et al. (2000) *J. Am. Chem. Soc.,* 122(36):8595-8602.

An oligonucleotide described herein can include a backbone that does not include a phosphorus atom, e.g., backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see, e.g., U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

An oligonucleotide as described herein can include one or more modifications selected from the group consisting of: pseudouridine, $N^1$-methylpseudouridine, and 5-methoxyuridine. For example, one or more $N^1$-methylpseudouridines can be incorporated into the RNA fragment to provide enhanced RNA stability and reduced immunogenicity in animal cells, such as mammalian cells (e.g., cells of human and mice). $N^1$-methylpseudouridine modifications can also be incorporated in combination with one or more 5-methylcytidines.

5'-Methylcytidine-5'-triphosphate (5-methyl-CTP), N6-methyl-ATP, as well as pseudo-UTP and 2-thio-UTP, have also been shown to reduce innate immune stimulation in culture and in vivo as illustrated in Kormann et al. (2011) *Nat. Biotechnol.,* 29:154-157 and Warren et al. (2010) *Cell Stem Cell,* 7(5):618-630. An oligonucleotide can incorporate modifications (e.g. pseudo-UTP) designed to bypass innate antiviral responses. See, e.g., Warren et al. (2010) *Cell Stem Cell,* 7(5):618-630.

Mimetics

An oligonucleotide described herein can be a nucleic acid mimetic. The term "mimetic" as it is applied to polynucleotides can include polynucleotides wherein only the furanose ring or both the furanose ring and the internucleotide linkage are replaced with non-furanose groups. Replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

An oligonucleotide described herein can be a polynucleotide mimetic based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. Morpholino-based polynucleotides are nonionic mimics of oligonucleotides, which are less likely to form undesired interactions with cellular proteins (Braasch et al. (2002) Biochemistry, 41(14): 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

An oligonucleotide described herein can be a polynucleotide mimetic referred to as cyclohexenyl nucleic acid (GeNA), where the furanose ring normally present in a DNA/RNA molecule is replaced with a cydohexenyl ring. GeNA DMT protected phosphoramidite monomers have been prepared and used for oligomeric compound synthesis following classical phosphoramidite chemistry. Fully modified GeNA oligonucleotides having specific positions modified with GeNA have been prepared and studied (see Wang et al. (2000) *J. Am. Chem. Soc.,* 122(36):8595-8602).

An oligonucleotide described herein can be a Locked Nucleic Acid (LNA), in which the 2'-hydroxyl group is linked to the 4' carbon atom of the sugar ring, forming a 2'-C, 4'-C-oxymethylene linkage, thereby forming a bicyclic sugar moiety. The linkage can be a methylene $(—CH_2—)_n$ group bridging the 2' oxygen atom and the 4' carbon atom wherein n is 1 or 2 (Singh et al. (1998) *Chem. Commun.,* 4:455-456). LNA and LNA analogs display very high duplex thermal stabilities with complementary DNA and RNA ($T_m$=+3 to +10° C.), stability towards 3'-exonucleolytic degradation, and good solubility properties. Potent and nontoxic antisense oligonucleotides containing LNAs are described in e.g., Wahlestedt et al. (2000) *Proc. Natl. Acad. Sci. U.S.A.,* 97(10):5633-5638. The synthesis and preparation of the LNA monomers adenine, cytosine, guanine, 5-methyl-cytosine, thymine, and uracil, along with their oligomerization, and nucleic acid recognition properties have been described (Koshkin et al. (1998) *Tetrahedron,* 54(14):3607-3630). LNAs and preparation thereof are also described in WO 98/39352 and WO 99/14226.

Modified Sugar Moieties

An oligonucleotide described herein can include one or more substituted sugar moieties including, for example, a sugar substituent group selected from: OH; F; O-, S-, or N-alkyl; O-, S-, or N-alkenyl; O-, S- or N-alkynyl; and O-alkyl-O-alkyl, wherein the alkyl, alkenyl and alkynyl may be substituted or unsubstituted C1 to C10 alkyl or C2 to C10 alkenyl and alkynyl. Particularly suitable are $O((CH_2)_nO)_mCH_3$, $O(CH_2)_nOCH_3$, $O(CH_2)_nNH_2$, $O(CH_2)CH_3$, $O(CH_2)_nONH_2$, and $O(CH_2)_nON((CH_2)_nCH_3)_2$, where n and m are from 1 to about 10. Other oligonucleotides include a suitable sugar substituent group selected from: C1 to C10 lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, a group for improving the pharmacodynamic properties of an oligonucleotide, and other substituents having similar properties. A suitable modification includes 2'-methoxyethoxy 2'-O—$CH_2$—$CH_2OCH_3$, also known as -2'-O-(2-methoxyethyl) or 2'-MOE) (Martin et al. (1995) *Helv. Chim. Acta.* 78(2):486-504) e.g., an alkoxyalkoxy group. A further suitable modification includes 2'-dimethylaminooxyethoxy, e.g., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), e.g., 2'-O—$CH_2$—O—$CH_2$—$N(CH_3)_2$.

Other suitable sugar substituent groups include methoxy (—O—$CH_3$), aminopropoxy (—O—$CH_2CH_2CH_2NH_2$), allyl (—$CH_2$—CH═$CH_2$), —O-allyl (—O—$CH_2$—CH═$CH_2$) and fluoro (F). 2'-sugar substituent groups may be in the arabino (up) position or ribo (down) position. A suitable 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

An RNA fragment according to any of the embodiments described herein can include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine (see, Komberg et al. (1980) *DNA Replication* ($2^{nd}$ ed.) (pp. 75-77). San Francisco, CA: W. H. Freeman & Co.; Gebeyehu et al. (1987) *Nucl. Acids Res.,* 15(11):4513-4534). A "universal" base known in the art, e.g. inosine, can also be included. 5-Me-C substitutions have been shown to increase nucleic acid duplex stability by 0.6-1.2° C. (Sanghvi (1993). *Antisense Research and Applications*. (pp. 276-278). Crooke, S. T. and Lebleu, B., (Eds.), Boca Raton, FL: CRC Press) and are embodiments of base substitutions.

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other a-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases include those disclosed in U.S. Pat. No. 3,687,808, those disclosed in Kroschwitz (Ed.) (1990). *The Concise Encyclopedia of Polymer Science and Engineering*, (pp. 858-859). Hoboken, N.J.: John Wiley & Sons, those disclosed by Englisch et al. (1991) *Angewandte Chemie International Edition,* 30(6):613-722, and those disclosed by Sanghvi (1993) Chapter 15*, Antisense Research and Applications*, (pp. 289-302), Crooke, S. T. and Lebleu, B. (Eds), Boca Raton, FL: CRC Press. Certain types of these nucleobases are particularly useful for increasing the binding affinity of the oligonucleotides of the disclosure. These include 5-substituted pyrimidines, 6-azapyrimidines and N-2, N-6 and —O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi (1993) *Antisense Research and Applications*. (pp. 276-278). Crooke and Lebleu, (Eds.), Boca Raton, FL: CRC Press) and are embodiments of base substitutions, even more particularly when combined with 2'-O-methoxyethyl sugar modifications.

An oligonucleotide according to any of the embodiments described herein comprising nucleobase modifications or substitutions may not have all positions uniformly modified. For example, an oligonucleotide may have a modification incorporated in a single nucleoside.

In some instances, the oligonucleotide includes a sequence of 5 to 15 (e.g., 6, 7, 8, 9, 10, 11, 12, 13, or 14) LNAs. In some instances, the oligonucleotide includes a sequence of 10 to 25 (e.g., 11, 12, 13, 14, 15, 16, 17, 18, 19, 20, 21, 22, 23, or 24) nucleotides having modifications at the 2' position of the sugar (e.g., 2' O-methyl).

Cap Conjugation

The m7G cap or a variant or analog thereof can be conjugated to the oligonucleotide via a linker. Any suitable linkers known in the art are included. Suitable linkers can include those that possess sufficient stability in vivo. Alkyl linkers such as —$NH(CH_2)_nC(O)$—, wherein n=2-20 can be used. These alkyl linkers may further be substituted by any non-sterically hindering group such as lower alkyl (e.g., C1-C6) lower acyl, halogen (e.g., Cl, Br), CN, $NH_2$, phenyl, etc. In another example, polyethylene glycol (PEG) can be used. About 10 to about 30 PEG subunits (e.g., about 12 to about 28, about 15 to about 25, or about 20 subunits) can be used for the conjugation. The type and length of the linker can be modified to adjust the editing window.

The cap-conjugated oligonucleotide can be chemically synthesized, such as through solid phase synthesis. An example of capped RNA prepared by solid-phase synthesis is described in Kadokura et al. *Tetrahedron Lett.* 2001; 42:8853-8856. Briefly, a 2,2,7-trimethylguanosine (TMG)-capped trinucleotide block of Ul snRNA with the structure $m_3^{2,2,7}G^{5'}pppAm^{2'}Um^{2'}A$ can be prepared, starting from a 5'-phosphorylated trimer synthesized by standard phosphoramidite chemistry. TMG-capping reaction can be carried out upon deprotection of all base-labile groups. Utilization of a novel, acid labile linker to the solid support can allow for subsequent release of the RNA. As another example, an RNA bearing a 5'-terminal TMG-capped pyrophosphate linkage on solid support is described in Ohkubo et al. *Bioorg Med Chem.* 2009; 17:4819-4824.

The m7G cap or a variant or analog thereof can be conjugated (e.g., via a linker) to the 5' end or the 3' end of the oligonucleotide, or can be conjugated to a nucleotide between the 5' and the 3' ends of the oligonucleotide.

III. Pharmaceutical Compositions and Administration

Some aspects of the present disclosure provide pharmaceutical preparations or compositions comprising the cap-conjugated oligonucleotides described herein. Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY).

Therapeutic compounds that are or include nucleic acids can be administered by any method suitable for administration of nucleic acid agents. These methods include gene guns, bio injectors, and skin patches as well as needle-free methods. Additionally, intranasal delivery is possible, as described in, inter alia, Hamajima et al., *Clin. Immunol. Immunopathol.,* 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

IV. Methods of Enhancing Protein Translation

Some embodiments disclosed herein provide compositions for and methods of enhancing protein translation in a cell, for example, by recruiting an m7G cap or a variant or analog thereof to the vicinity of a desired start codon in an mRNA. By bringing the m7G cap or a variant or analog thereof closer to the desired start codon as compared to the endogenous m7G cap of the mRNA, translation initiation proteins can be recruited to the vicinity of the start codon, thereby initiating translation. The methods include contacting the cell with a cap-conjugated oligonucleotide comprising an m7G cap or a variant or analog thereof conjugated to an oligonucleotide, where the oligonucleotide is capable of specifically hybridizing with a target sequence in an mRNA. The oligonucleotide can include one or more modifications (e.g., any of the modifications disclosed herein or known in the art) that, e.g., reduce sensitivity to cellular nucleases and/or increase stability. The m7G cap or a variant or analog thereof can be conjugated (e.g., through a linker) to the oligonucleotide at the 5' end, 3' end or at any of the nucleotides between the 5' and 3' ends. The m7G cap or a variant or analog thereof can include one or more modifications that can, e.g., enhance EIF4E association and/or to prevent further conjugation from the 3' hydroxyl group.

Methods of measuring levels of protein translation are known in the art. Exemplary methods include western blot, mass spectrometry, antibody staining, and FACS analysis. In some instances, a reporter gene that encodes a reporter molecule can be linked to the target mRNA, which can be translated together with the target mRNA. Levels of target mRNA translation can then be measured based on the levels of the reporter molecule. Exemplary reporter molecules include fluorescent or luminescent proteins (e.g., GFP, dsRed, YFP, etc.) and enzymes (e.g., luciferase, beta-galactosidase, and chloramphenicol acetyltransferase). Expression of the reporter molecules can be detected using methods known in the art. For example, to detect fluorescent or luminescent proteins, fluorescent microscopes can be used. The respective substrates for the enzymes can be applied for detection.

In some embodiments, enhancing translation or increasing or upregulating gene expression refers to an increase in the amount of peptide translated from the target mRNA as compared to a control. In some embodiments, the control includes a level of peptide translated from the target mRNA in the absence of the capped-oligonucleotide compositions and methods. In some embodiments, the control includes the level of the peptide translated from the target mRNA prior to addition of the compositions disclosed herein. In some embodiments, translation is increased about 1.1 fold, about 1.2 fold, about 1.3 fold, about 1.4 fold, about 1.5 fold, about 1.6 fold, about 1.7 fold, about 1.8 fold, about 1.9 fold, about 2 fold, about 2.5 fold, about 3 fold, about 4 fold, about 5 fold, about 6 fold, about 7 fold, about 8 fold, about 9 fold, about 10 fold, about 20 fold, about 50 fold, about 100 fold, about 1000 fold, or about 10,000 fold relative to the control. The amount of peptide translated can be determined by any method known in the art.

In certain embodiments, methods of modulating protein translation are useful for treating patients afflicted with a disease or disorder. In one embodiment, methods of using the cap-conjugated oligonucleotide compositions disclosed herein are useful for treating haploinsufficiency. Exemplary haploinsufficiency diseases or disorders include, without limitation, Autosomal dominant Retinitis Pigmentosa (RP11) caused by mutations in PRPF31, Autosomal dominant Retinitis Pigmentosa (RP31) caused by mutations in TOPORS, Frontotemporal dementia caused by mutations in GRN, DeVivo Syndrome (Glut1 deficiency) caused by mutations in SLC2A1, Dravet syndrome caused by mutations in SCN1A.

In another embodiment, methods of using the cap-conjugated oligonucleotide compositions disclosed herein for treating diseases or disorders involving mutations which lead to introduction of a premature termination codon (PTC) resulting in degradation from mutant allele or loss of function of the protein (or less protein to be produced) are contemplated herein.

In another embodiment, methods of translation enhancement using the cap-conjugated oligonucleotide compositions disclosed herein are useful for treating cancer. In one embodiment, the methods can be used for upregulating protein expression of tumor suppressor genes (TSG) in tissue predisposed to cancer due to hereditary (or acquired) mutations of TSG. In another embodiment, the methods can be used for upregulating protein expression from genes that would prevent cancer from metastasizing (e.g. angiogenesis genes). In another embodiment, the methods can be used for upregulating protein expression from genes that would result in the cancer being more susceptible to follow-up treatments. In another embodiment, the methods can be used for translational enhancement to prevent cancer evasion of the immune system.

As used herein, the "administration" of the compositions disclosed herein to a subject includes any route of introducing or delivering to a subject the agent to perform its intended function. Administration can be carried out by any suitable route, including orally, intranasally, intraocularly, ophthalmically, parenterally (intravenously, intramuscularly, intraperitoneally, or subcutaneously), or topically. Administration includes self-administration and the administration by another.

In some aspects, the disclosure provides a method of treating a disease or disorder comprising administering to a subject a therapeutically effective amount of a cap-conjugated oligonucleotide composition(s) of the disclosure, thereby enhancing translation of a target mRNA in the subject. In some embodiments, the target mRNA is involved in the etiology of a disease or condition in the subject.

In some embodiments of the methods described herein, the subject or patient is an animal. In some embodiments, the subject is a mammal. In some embodiments, the mammal is a bovine, equine, porcine, canine, feline, simian, murine, or human. In some embodiments, the subject is a human.

In some embodiments of the compositions and methods of the disclosure, a disease or disorder of the disclosure includes, but is not limited to, a genetic disease or disorder. In some embodiments, the genetic disease or disorder is a single-gene disease or disorder. In some embodiments, the single-gene disease or disorder is an autosomal dominant disease or disorder, an autosomal recessive disease or disorder, an X-chromosome linked (X-linked) disease or disorder, an X-linked dominant disease or disorder, an X-linked recessive disease or disorder, a Y-linked disease or disorder or a mitochondrial disease or disorder. In some embodiments, the genetic disease or disorder is a multiple-gene disease or disorder. In some embodiments, the genetic disease or disorder is a multiple-gene disease or disorder. In some embodiments, the single-gene disease or disorder is an autosomal dominant disease or disorder including, but not limited to, Huntington's disease, neurofibromatosis type 1, neurofibromatosis type 2, Marfan syndrome, hereditary nonpolyposis colorectal cancer, hereditary multiple exostoses, Von Willebrand disease, and acute intermittent porphyria. In some embodiments, the single-gene disease or disorder is an autosomal recessive disease or disorder including, but not limited to, Albinism, Medium-chain acyl-CoA dehydrogenase deficiency, cystic fibrosis, sickle-cell disease, Tay-Sachs disease, Niemann-Pick disease, spinal muscular atrophy, and Roberts syndrome. In some embodiments, the single-gene disease or disorder is X-linked disease or disorder including, but not limited to, muscular dystrophy, Duchenne muscular dystrophy, Hemophilia, Adrenoleukodystrophy (ALD), Rett syndrome, and Hemophilia A. In some embodiments, the single-gene disease or disorder is a mitochondrial disorder including, but not limited to, Leber's hereditary optic neuropathy.

In some embodiments of the compositions and methods of the disclosure, a disease or disorder of the disclosure includes, but is not limited to, an immune disease or disorder. In some embodiments, the immune disease or disorder is an immunodeficiency disease or disorder including, but not limited to, B-cell deficiency, T-cell deficiency, neutropenia, asplenia, complement deficiency, acquired immunodeficiency syndrome (AIDS) and immunodeficiency due to medical intervention (immunosuppression as an intended or adverse effect of a medical therapy). In some embodiments, the immune disease or disorder is an autoimmune disease or disorder including, but not limited to, Achalasia, Addison's disease, Adult Still's disease, Agammaglobulinemia, Alopecia areata, Amyloidosis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Balo disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNJJ), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Vogt-Koyanagi-Harada Disease, or Wegener's granulomatosis.

In some embodiments of the compositions and methods of the disclosure, a disease or disorder of the disclosure includes, but is not limited to, an inflammatory disease or disorder.

In some embodiments of the compositions and methods of the disclosure, a disease or disorder of the disclosure includes, but is not limited to, a metabolic disease or disorder.

In some embodiments of the compositions and methods of the disclosure, a disease or disorder of the disclosure includes, but is not limited to, a degenerative or a progressive disease or disorder. In some embodiments, the degenerative or a progressive disease or disorder includes, but is not limited to, amyotrophic lateral sclerosis (ALS), Huntington's disease, Alzheimer's disease, and aging.

In some embodiments of the compositions and methods of the disclosure, a disease or disorder of the disclosure includes, but is not limited to, an infectious disease or disorder.

In some embodiments of the compositions and methods of the disclosure, a disease or disorder of the disclosure includes, but is not limited to, a pediatric or a developmental disease or disorder.

In some embodiments of the compositions and methods of the disclosure, a disease or disorder of the disclosure includes, but is not limited to, a cardiovascular disease or disorder.

In some embodiments of the compositions and methods of the disclosure, a disease or disorder of the disclosure includes, but is not limited to, a proliferative disease or disorder. In some embodiments, the proliferative disease or disorder is a cancer. In some embodiments, the cancer includes, but is not limited to, Acute Lymphoblastic Leukemia (ALL), Acute Myeloid Leukemia (AML), Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer, Gastrointestinal Carcinoid Tumors, Astrocytomas, Atypical Teratoid/Rhabdoid Tumor, Central Nervous System (Brain Cancer), Basal Cell Carcinoma, Bile Duct Cancer, Bladder Cancer, Bone Cancer, Ewing Sarcoma, Osteosarcoma, Malignant Fibrous Histiocytoma, Brain Tumors, Breast Cancer, Burkitt Lymphoma, Carcinoid Tumor, Carcinoma, Cardiac (Heart) Tumors, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ, Embryonal Tumors, Endometrial Cancer (UterineCancer), Ependymoma, Esophageal Cancer, Esthesioneuroblastoma (Head and Neck Cancer), Ewing Sarcoma (Bone Cancer), Extracranial Germ Cell Tumor, Extragonadal Germ Cell Tumor, Eye Cancer, Childhood Intraocular Melanoma, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST) (Soft Tissue Sarcoma), Childhood Gastrointestinal Stromal Tumors, Germ Cell Tumors, Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell and Small Cell), Childhood Lung Cancer, Lymphoma, Male Breast Cancer, Malignant Fibrous Histiocytoma of Bone and Osteosarcoma, Melanoma, Merkel Cell Carcinoma (Skin Cancer), Mesothelioma, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer, Osteosarcoma and Malignant Fibrous Histiocytoma of Bone, Ovarian Cancer, Pancreatic Cancer, Pancreatic Neuroendocrine Tumors (Islet Cell Tumors), Papillomatosis, Paraganglioma, Parathyroid Cancer, Penile Cancer, Pharyngeal Cancer (Head and Neck Cancer), Pheochromocytoma, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Childhood (Soft Tissue Sarcoma), Salivary Gland Cancer (Head and Neck Cancer), Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Uterine Sarcoma, Sezary Syndrome, Lymphoma, Skin Cancer, Small Cell Lung Cancer, Small Intestine Cancer, Soft Tissue Sarcoma, Squamous Cell Carcinoma of the Skin, Squamous Neck Cancer, Stomach (Gastric) Cancer, T-Cell Lymphoma, Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter, Renal Cell Cancer, Urethral Cancer, Uterine Sarcoma, Vaginal Cancer, Vascular Tumors (Soft Tissue Sarcoma), Vulvar Cancer, Wilms Tumor and Other Childhood Kidney Tumors.

In some embodiments of the methods of the disclosure, a subject of the disclosure has been diagnosed with the disease or disorder. In some embodiments, the subject of the disclosure presents at least one sign or symptom of the disease or disorder. In some embodiments, the subject has a biomarker predictive of a risk of developing the disease or disorder. In some embodiments, the biomarker is a genetic mutation.

In some embodiments of the methods of the disclosure, a subject of the disclosure is female. In some embodiments of the methods of the disclosure, a subject of the disclosure is male. In some embodiments, a subject of the disclosure has two XX or XY chromosomes. In some embodiments, a subject of the disclosure has two XX or XY chromosomes and a third chromosome, either an X or a Y.

In some embodiments of the methods of the disclosure, a subject of the disclosure is a neonate, an infant, a child, an adult, a senior adult, or an elderly adult. In some embodiments of the methods of the disclosure, a subject of the disclosure is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days old. In some embodiments of the methods of the disclosure, a subject of the disclosure is at least 1, 2, 3, 4, 5, 6, 7, 8, 9, 10, 11 or 12 months old. In some embodiments of the methods of the disclosure, a subject of the disclosure is at least 1, 2, 3, 4, 5, 6, 7, 8, 9, 10, 15, 20, 25, 30, 35, 40, 45, 50, 55, 60, 65, 70, 75, 80, 85, 90, 95, 100 or any number of years or partial years in between of age.

In some embodiments of the methods of the disclosure, a subject of the disclosure is a mammal. In some embodiments, a subject of the disclosure is a non-human mammal.

In some embodiments of the methods of the disclosure, a subject of the disclosure is a human.

In some embodiments of the methods of the disclosure, a therapeutically effective amount comprises a single dose of a composition of the disclosure. In some embodiments, a therapeutically effective amount comprises a therapeutically effective amount comprises at least one dose of a composition of the disclosure. In some embodiments, a therapeutically effective amount comprises a therapeutically effective amount comprises one or more dose(s) of a composition of the disclosure. In some embodiments of the methods of the disclosure, a therapeutically effective amount eliminates a sign or symptom of the disease or disorder. In some embodiments, a therapeutically effective amount reduces a severity of a sign or symptom of the disease or disorder.

In some embodiments of the methods of the disclosure, a therapeutically effective amount eliminates the disease or disorder.

In some embodiments of the methods of the disclosure, a therapeutically effective amount prevents an onset of a disease or disorder. In some embodiments, a therapeutically effective amount delays the onset of a disease or disorder. In some embodiments, a therapeutically effective amount reduces the severity of a sign or symptom of the disease or disorder. In some embodiments, a therapeutically effective amount improves a prognosis for the subject.

In some embodiments of the methods of the disclosure, a composition of the disclosure is administered to the subject systemically. In some embodiments, the composition of the disclosure is administered to the subject by an intravenous route. In some embodiments, the composition of the disclosure is administered to the subject by an injection or an infusion.

In some embodiments of the methods of the disclosure, a composition of the disclosure is administered to the subject locally. In some embodiments, the composition of the disclosure is administered to the subject by an intraosseous, intraocular, intracerebrospinal, or intraspinal route. In some embodiments, the composition of the disclosure is administered directly to the cerebral spinal fluid of the central nervous system. In some embodiments, the composition of the disclosure is administered directly to a tissue or fluid of the eye and does not have bioavailability outside of ocular structures. In some embodiments, the composition of the disclosure is administered to the subject by an injection or an infusion.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Figure 1B:
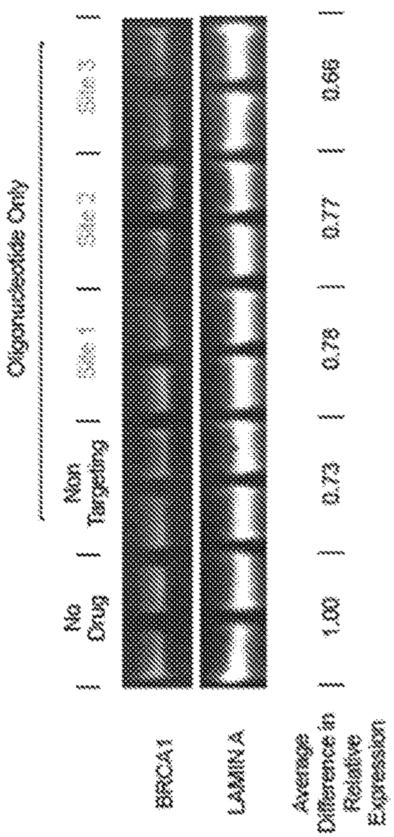
Figure 1C:
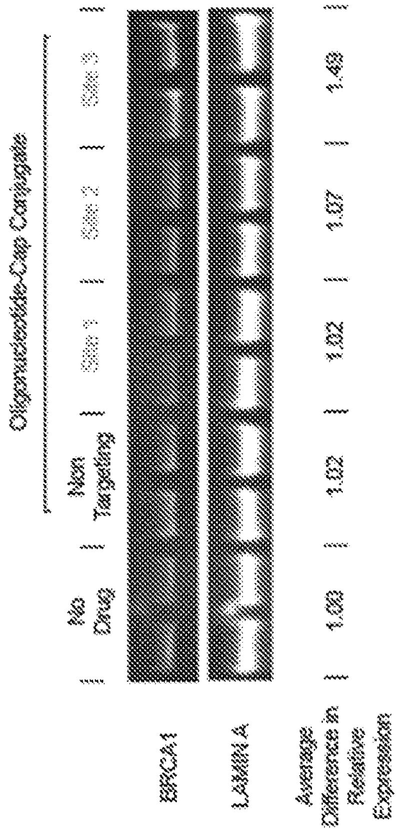

Example 1: Recruitment of m7G Cap to Target Start Codons Using Short Complementary Oligonucleotide Sequences Cap-conjugated synthetic oligonucleotides were designed to target sequences in the BRCA1 mRNA. Three cap-conjugated oligonucleotides capable of hybridizing with three different sequences surrounding a start codon of the BRCA1 coding sequence were designed (FIG. 1A). A cap-conjugated oligonucleotide that did not target any sequence in the BRCA1 mRNA (non-targeting) was used as control. Oligonucleotides corresponding to the four cap-conjugated oligonucleotides described above, but do not contain the cap structure ("Oligonucleotide only") were also used as controls. As shown in FIGS. 1B and 1C, in contrast to oligonucleotide only, cap-conjugated oligonucleotides targeting different sequences (site 1, site 2, and site 3) in the BRCA1 mRNA resulted in differential changes in BRCA1 protein expression. Targeting certain sequences (e.g., site 2 and site 3) resulted in increased BRCA1 protein as compared to non-targeting cap-conjugated oligonucleotides.

Additional Embodiments

Embodiment 1: A conjugated m7G cap having the structure:

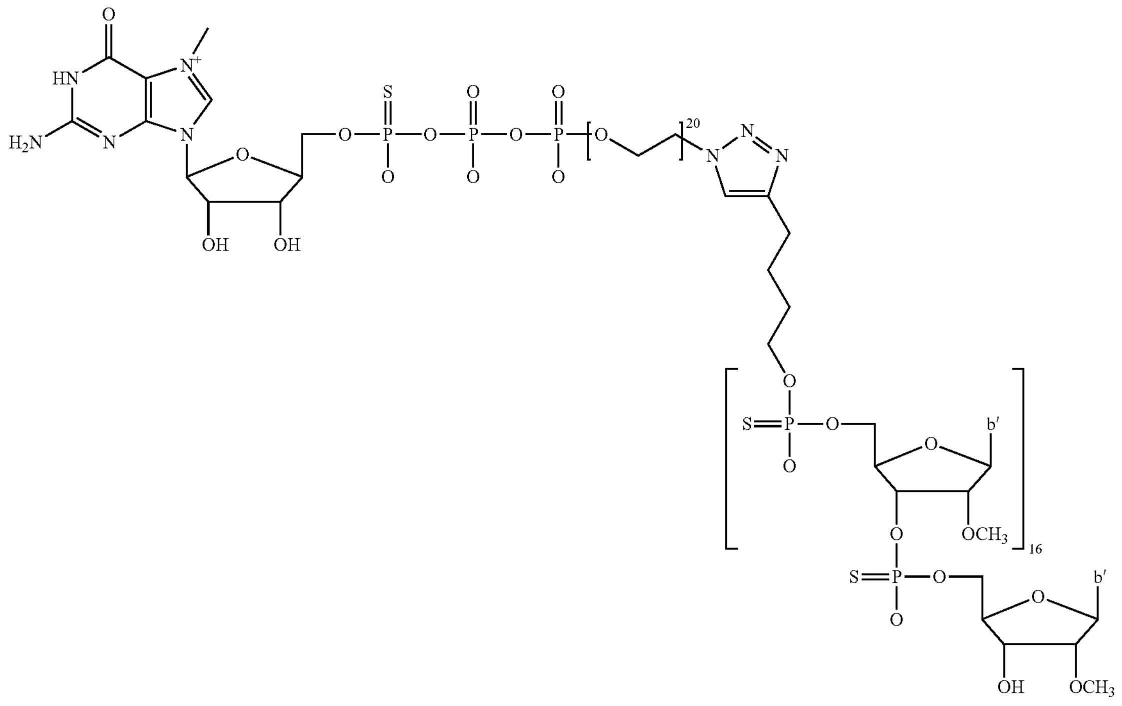

wherein b' comprises a sequence complementary to a target sequence in a messenger RNA.

Embodiment 2: The conjugated m7G cap of Embodiment 1, wherein the target sequence is proximal to a target start codon of the messenger RNA relative to a 5' m7G cap of the messenger RNA.

Embodiment 3: The conjugated m7G cap of Embodiment 1, wherein the target sequence comprises the target start codon of the messenger RNA.

Embodiment 4: The conjugated m7G cap of Embodiment 2, wherein the 5' end of the target sequence is upstream to the target start codon of the messenger RNA.

Embodiment 5: The conjugated m7G cap of Embodiment 2, wherein the 5' end of the target sequence is downstream to the target start codon of the messenger RNA.

Embodiment 6: A conjugated m7G cap having the structure:

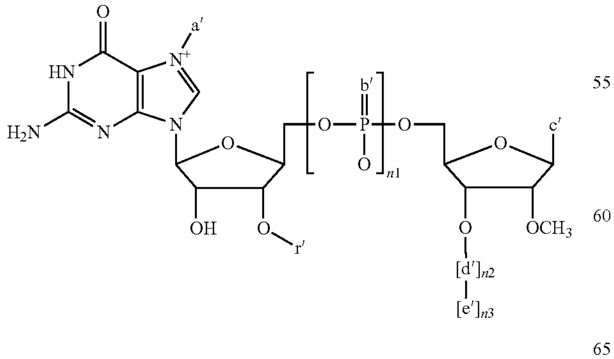

wherein r' is methyl or a functional group configured to prevent further extension, a' is methyl or a functional group configured to enhance association with an EIF4E protein, b' is oxygen or sulfur, c' is a nitrogenous base, d' is a linker, and e' is a targeting moiety.

Embodiment 7: The conjugated m7G cap of Embodiment 6, wherein c' is a nitrogenous base selected from the group consisting of adenine, guanine, cytosine, thymine and uracil.

Embodiment 8: The conjugated m7G cap of Embodiment 7, wherein d' is a biocompatible polymeric linker.

Embodiment 9: The conjugated m7G cap of Embodiment 8, wherein d' is a polyethlene glycol (PEG) comprising fewer than about 30 subunits.

Embodiment 10: The conjugated m7G cap of Embodiment 6, wherein e' comprises a nucleic acid sequence complementary to a target sequence in a messenger RNA.

Embodiment 11: The conjugated m7G cap of Embodiment 10, wherein the target sequence is proximal to a target start codon of the messenger RNA relative to a 5' m7G cap of the messenger RNA.

Embodiment 12: The conjugated m7G cap of Embodiment 10, wherein the target sequence comprises the target start codon of the messenger RNA.

Embodiment 13: The conjugated m7G cap of Embodiment 11, wherein the 5' end of the target sequence is upstream to the target start codon of the messenger RNA.

Embodiment 14: The conjugated m7G cap of Embodiment 11, wherein the 5' end of the target sequence is downstream to the target start codon of the messenger RNA.

Embodiment 15: The conjugated m7G cap of Embodiment 10, wherein the nucleic acid sequence comprises one or more phosphorothioate modification(s), and wherein the nucleic acid sequence comprises about 10 to about 25 nucleotides.

Embodiment 16: The conjugated m7G cap of Embodiment 10, wherein the nucleic acid sequence comprises one or more locked nucleic acid(s), and wherein the nucleic acid sequence comprises about 5 to about 15 nucleotides.

Embodiment 17: The conjugated m7G cap of Embodiment 10, wherein the nucleic acid sequence comprises one or more phosphorothiorate modification(s) and one or more locked nucleic acid(s), and wherein the nucleic acid sequence comprises fewer than about 25 nucleotides.

Embodiment 18: The conjugated m7G cap of Embodiment 6, wherein n1 is fewer than about 4.

A conjugated m7G cap having the structure:

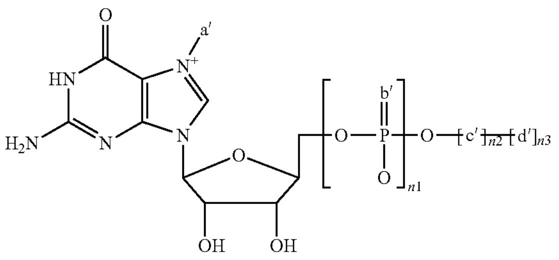

Wherein a' is methyl or a functional group configured to enhance association with an EIF4E protein, b' is oxygen or sulfur, c' is a linker, and d' is a targeting moiety.

Embodiment 19: The conjugated m7G cap of Embodiment 18, wherein c' is a biocompatible polymeric linker.

Embodiment 20: The conjugated m7G cap of Embodiment 19, wherein c' is a polyethlene glycol (PEG) comprising fewer than about 30 subunits.

Embodiment 21: The conjugated m7G cap of Embodiment 18, wherein d' comprises a nucleic acid sequence complementary to a target sequence in a messenger RNA.

Embodiment 22: The conjugated m7G cap of Embodiment 21, wherein the target sequence is proximal to a target start codon of the messenger RNA relative to a 5' m7G cap of the messenger RNA.

Embodiment 23: The conjugated m7G cap of Embodiment 21, wherein the target sequence comprises the target start codon of the messenger RNA.

Embodiment 24: The conjugated m7G cap of Embodiment 22, wherein the 5' end of the target sequence is upstream to the target start codon of the messenger RNA.

Embodiment 25: The conjugated m7G cap of Embodiment 22, wherein the 5' end of the target sequence is downstream to the target start codon of the messenger RNA.

Embodiment 26: The conjugated m7G cap of Embodiment 21, wherein the nucleic acid sequence comprises one or more phosphorothiorate modification(s), and wherein the nucleic acid sequence comprises about 10 to about 25 nucleotides.

Embodiment 27: The conjugated m7G cap of Embodiment 21, wherein the nucleic acid sequence comprises one or more locked nucleic acid(s), and wherein the nucleic acid sequence comprises about 5 to about 15 nucleotides.

Embodiment 28: The conjugated m7G cap of Embodiment 21, wherein the nucleic acid sequence comprises one or more phosphorothiorate modification(s) and one or more locked nucleic acid(s), and wherein the nucleic acid sequence comprises fewer than about 25 nucleotides.

Embodiment 29: The conjugated m7G cap of Embodiment 18, wherein n1 is fewer than about 4.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A cap-conjugated oligonucleotide comprising an m7G cap or a variant or analog thereof conjugated to an oligonucleotide, wherein the oligonucleotide is at least 80% complementary to a target sequence in an RNA molecule, wherein the 5' end of the target sequence is between 50 nucleotides upstream of the first nucleotide of a target start codon of the RNA molecule and 50 nucleotides downstream of the last nucleotide of the target start codon, and wherein the m7G cap or a variant or analog thereof comprises a structure of

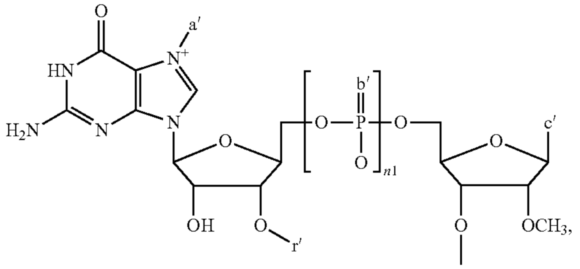

wherein a' is methyl, (4-Chlorophenyl-ethyl)-, or (4-Fluorophenyl-ethyl)-, b' is oxygen, sulfur, or boron, and n1 is equal to or fewer than 4.

2. The cap-conjugated oligonucleotide of claim 1, wherein the RNA molecule is a messenger RNA (mRNA).

3. The cap-conjugated oligonucleotide of claim 2, wherein the mRNA comprises the target start codon, and wherein the 5' end of the target sequence is upstream of the target start codon.

4. The cap-conjugated oligonucleotide of claim 2, wherein the mRNA comprises the target start codon, and wherein the 5' end of the target sequence is downstream of the target start codon.

5. The cap-conjugated oligonucleotide of claim 1, wherein the oligonucleotide comprises about 5 to about 30 nucleotides.

6. The cap-conjugated oligonucleotide of claim 1, wherein the oligonucleotide comprises one or more backbone modifications.

7. The cap-conjugated oligonucleotide of claim 1, wherein the oligonucleotide comprises one or more locked nucleic acids (LNAs).

8. The cap-conjugated oligonucleotide of claim 1, wherein the oligonucleotide comprises one or more substituted sugar moieties.

9. The cap-conjugated oligonucleotide of claim 8, wherein the oligonucleotide comprises one or more nucleotides modified at the 2' position of the sugar.

10. The cap-conjugated oligonucleotide of claim 1, wherein the m7G cap or a variant or analog thereof is conjugated to the oligonucleotide via a linker.

11. The cap-conjugated oligonucleotide of claim 1, wherein two or more m7G caps or a variant or analog thereof are conjugated to the oligonucleotide.

12. A composition comprising the cap-conjugated oligonucleotide of claim 1 and a pharmaceutically acceptable carrier.

13. A cap-conjugated oligonucleotide comprising an m7G cap or a variant or analog thereof conjugated to an oligonucleotide, wherein the oligonucleotide is at least 80% complementary to a target sequence in an RNA molecule, wherein the target sequence is between 50 nucleotides upstream of the first nucleotide of a target start codon of the RNA molecule and 50 nucleotides downstream of the last nucleotide of the target start codon, and wherein the m7G cap or a variant or analog thereof comprises a structure of

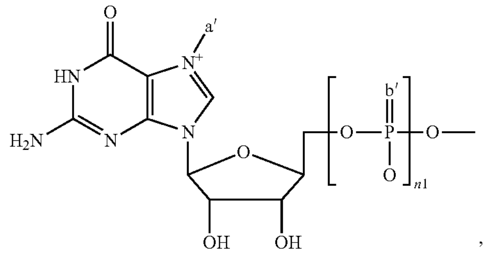

, wherein a' is methyl, (4-Chlorophenyl-ethyl)-, or (4-Fluorophenyl-ethyl)-, r' is methyl or a functional group configured to prevent further extension, b' is oxygen, sulfur, or boron, c' is a nitrogenous base, and n1 is equal to or fewer than 4.

14. The cap-conjugated oligonucleotide of claim 13, wherein the RNA molecule is a messenger RNA (mRNA).

15. The cap-conjugated oligonucleotide of claim 14, wherein the mRNA comprises the target start codon, and wherein the 5' end of the target sequence is upstream of the target start codon.

16. The cap-conjugated oligonucleotide of claim 14, wherein the mRNA comprises the target start codon, and wherein the 5' end of the target sequence is downstream of the target start codon.

17. The cap-conjugated oligonucleotide of claim 13, wherein the oligonucleotide comprises about 5 to about 30 nucleotides.

18. The cap-conjugated oligonucleotide of claim 13, wherein the oligonucleotide comprises one or more backbone modifications.

19. The cap-conjugated oligonucleotide of claim 13, wherein the oligonucleotide comprises one or more locked nucleic acids (LNAs).

20. The cap-conjugated oligonucleotide of claim 13, wherein the oligonucleotide comprises one or more substituted sugar moieties.

21. The cap-conjugated oligonucleotide of claim 20, wherein the oligonucleotide comprises one or more nucleotides modified at the 2' position of the sugar.

22. The cap-conjugated oligonucleotide of claim 13, wherein the m7G cap or a variant or analog thereof is conjugated to the oligonucleotide via a linker.

23. The cap-conjugated oligonucleotide of claim 13, wherein two or more m7G caps or a variant or analog thereof are conjugated to the oligonucleotide.

24. A composition comprising the cap-conjugated oligonucleotide of claim 13 and a pharmaceutically acceptable carrier.

* * * * *